United States Patent
Basu

(10) Patent No.: US 11,386,999 B2
(45) Date of Patent: Jul. 12, 2022

(54) MULTI-MODEL MEMBER OUTREACH SYSTEM

(71) Applicant: CollectiveHealth, Inc., San Francisco, CA (US)

(72) Inventor: Sanjay Basu, San Francisco, CA (US)

(73) Assignee: CollectiveHealth, Inc., San Francisco, CA (US)

( * ) Notice: Subject to any disclaimer, the term of this patent is extended or adjusted under 35 U.S.C. 154(b) by 0 days.

(21) Appl. No.: 16/881,981

(22) Filed: May 22, 2020

(65) Prior Publication Data

US 2021/0241907 A1 Aug. 5, 2021

Related U.S. Application Data

(60) Provisional application No. 62/969,573, filed on Feb. 3, 2020.

(51) Int. Cl.
| | |
|---|---|
| *G16H 10/60* | (2018.01) |
| *G06N 20/20* | (2019.01) |
| *G06Q 40/08* | (2012.01) |
| *G16H 50/30* | (2018.01) |
| *G16H 50/20* | (2018.01) |
| *G06Q 30/02* | (2012.01) |
| *G06Q 10/10* | (2012.01) |
| *G06N 5/04* | (2006.01) |

(52) U.S. Cl.
CPC ............. *G16H 50/20* (2018.01); *G06N 5/04* (2013.01); *G06N 20/20* (2019.01); *G06Q 10/10* (2013.01); *G06Q 30/0203* (2013.01); *G06Q 30/0205* (2013.01); *G06Q 30/0206* (2013.01); *G06Q 40/08* (2013.01); *G16H 10/60* (2018.01); *G16H 50/30* (2018.01)

(58) Field of Classification Search
CPC ...................................... G06Q 40/08
See application file for complete search history.

(56) References Cited

U.S. PATENT DOCUMENTS

| | | | |
|---|---|---|---|
| 2008/0147441 A1 | 6/2008 | Kil | |
| 2008/0177567 A1* | 7/2008 | Friedlander | G16Z 99/00 705/2 |

(Continued)

OTHER PUBLICATIONS

J Rocca, Ensemble methods: bagging, boosting and stacking, Apr. 22, 2019, Towards Data Science (Year: 2019).*

(Continued)

*Primary Examiner* — Christopher L Gilligan
*Assistant Examiner* — Karen A Hranek
(74) *Attorney, Agent, or Firm* — Lee & Hayes, P.C.

(57) ABSTRACT

Member outreach services to be offered to members of a health plan based on predictions generated by a prediction engine using data associated with the members. The prediction engine can include an ensemble of different base predictive models, and the prediction engine can use a weighted combination of base predictions produced by the different base predictive models to generate a final prediction associated with a member. A representative can attempt to contact the member based on an outreach ticket associated with the final prediction. The representative can also provide ticket feedback associated with the outreach, and the prediction engine can use the ticket feedback to adjust the weights associated with the different base predictive models.

20 Claims, 7 Drawing Sheets

(56) References Cited

U.S. PATENT DOCUMENTS

| | | | | |
|---|---|---|---|---|
| 2009/0138285 A1* | 5/2009 | Denberg | G06Q 10/109 | 705/3 |
| 2010/0004947 A1* | 1/2010 | Nadeau | G16H 50/20 | 705/3 |
| 2011/0119212 A1* | 5/2011 | De Bruin | A61B 5/00 | 706/12 |
| 2013/0096934 A1* | 4/2013 | Vaccaro | G16H 50/30 | 705/2 |
| 2014/0100884 A1* | 4/2014 | Hamilton | G06Q 10/06395 | 705/3 |
| 2016/0035040 A1* | 2/2016 | Young | G06Q 40/08 | 705/4 |
| 2016/0048766 A1* | 2/2016 | McMahon | G06Q 10/04 | 706/12 |
| 2016/0125143 A1* | 5/2016 | Stadler | G16H 50/30 | 705/3 |
| 2016/0358282 A1* | 12/2016 | Gopal | G16H 10/60 | |
| 2017/0061091 A1* | 3/2017 | McElhinney | G16H 40/67 | |
| 2017/0177801 A1* | 6/2017 | Ryan | G06F 19/324 | |
| 2017/0206319 A1* | 7/2017 | Attanapola | G06F 19/3481 | |
| 2019/0156955 A1* | 5/2019 | Winlo | G16H 50/30 | |
| 2019/0172564 A1* | 6/2019 | Chandra | G06F 16/24522 | |
| 2020/0012897 A1* | 1/2020 | Sreenivasan | G06K 9/6263 | |
| 2020/0184284 A1* | 6/2020 | Lim | G06N 3/08 | |
| 2020/0251205 A1* | 8/2020 | Li | G06N 20/00 | |

OTHER PUBLICATIONS

The PCT Search Report and Written Opinion dated May 3, 2021 for PCT application No. PCT/US21/14743, 14 pages.

* cited by examiner

MULTI-MODEL MEMBER OUTREACH SYSTEM

RELATED APPLICATIONS

This U.S. patent application claims priority to U.S. Provisional Patent Application No. 62/969,573, entitled "MULTI-MODEL MEMBER RISK PREDICTION AND FEEDBACK," filed on Feb. 3, 2020, the entirety of which is incorporated herein by reference.

BACKGROUND

Administrators can offer and manage health plans that provide one or more benefits to members of the health plans. For example, a health plan can be a health insurance plan that fully, or partially, covers the costs of medical services for members of the health insurance plan. In some examples, an administrator can administer a health plan on behalf of a sponsor, such as an employer that offers a health plan to its employees and/or their families. In this example, the administrator may be a third party that administers the health plan for the employer, and members may be the employees, and/or family members of the employee, that are covered by the health plan.

An administrator can also offer member outreach services to members of a health plan. For example, member outreach services may help members find healthcare services, help members make healthcare appointments, help members find transportation for healthcare appointments, educate members about medical conditions, educate members about prescriptions or other medical treatments, and/or otherwise assist members in overcoming hurdles in obtaining healthcare services.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
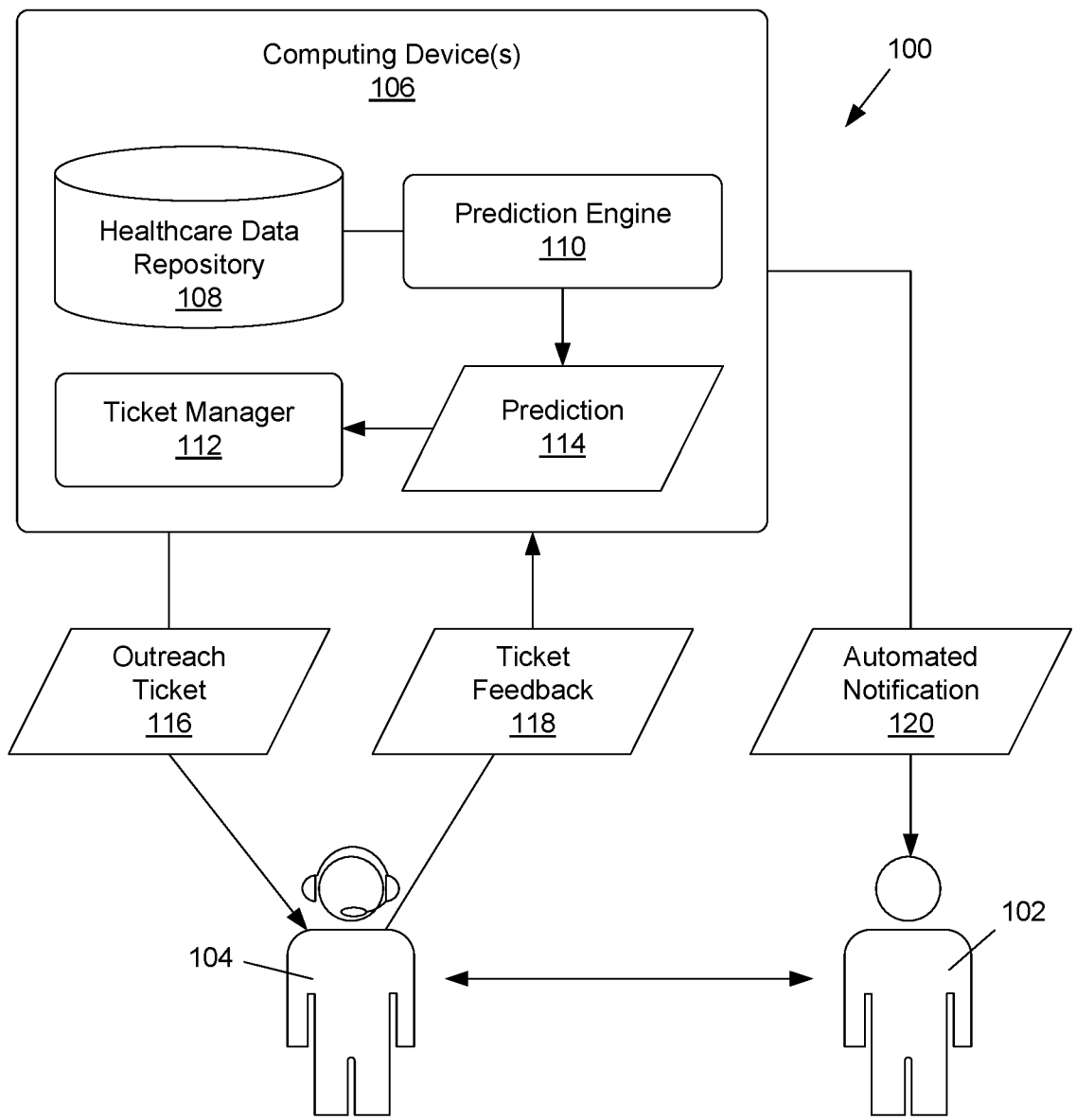
FIG. 1 depicts an example of a member outreach system.

The systems and methods described herein are associated with predictive models that are configured to generate predictions indicating when members of a health plan may benefit from member outreach services. The health plan can be an insurance plan, or other benefit plan, that provides one or more benefits to members of the health plan. For example, a health plan can provide benefits that fully or partially cover the costs of healthcare services for members of the health plan.

A health plan can be offered and/or managed by an administrator. As an example, the administrator may provide information about the health plan to members and potential members. As another example, the administrator may adjudicate healthcare claims associated with members of the health plan, when such healthcare claims are submitted by members, medical providers, or other entities.

An administrator may also, or alternately, offer member outreach services to members. For example, representatives of an administrator can contact members to help the members find in-person healthcare services, help the members make healthcare appointments, help the members find transportation to and from healthcare appointments, educate members about their conditions, treatments, or medications, and/or otherwise assist members in overcoming hurdles in obtaining healthcare services.

In some examples, member outreach services may be particularly beneficial to "high cost" members and/or "rising risk" members of a health plan. High cost members can be members who are predicted to incur relatively high healthcare expenses over a period of time. Rising risk members can, in some examples, be members whose healthcare expenses are predicted to increase during a future time period, relative to previous time periods. Rising risk members may also, or alternatively, be members whose risks of being admitted or readmitted to a hospital or other healthcare facility are predicted to increase, whose utilization of healthcare services are predicted to increase, whose pharmaceutical usage is predicted to advance to more expensive medications and/or to medications with increased side effects, whose suffering levels are predicted to increase, whose mortality risks are predicted to increase, and/or whose risk in any other category is predicted to increase during a future time period. For such high cost and/or rising risk members, member outreach services may prompt early medical intervention or other proactive steps, for instance before such high or rising healthcare expenses are incurred or other detrimental effects are experienced. Accordingly, member outreach services may proactively improve the health of a member and/or reduce healthcare expenses ultimately incurred by the member.

However, it can be difficult to identify which members are high cost or rising risk members that should be contacted to offer member outreach services. Some administrators and insurers use risk adjustment models to predict future costs of members, and can accordingly use predictions generated by the risk adjustment models to identify high cost and/or rising risk members. However, conventional risk adjustment models generally use relatively simple linear regression algorithms to estimate a member's future costs. As an example, a typical conventional risk adjustment model may multiply an age of a member by a first value to generate a first cost estimate, a tobacco smoking status of the member by a second value to generate a second cost estimate, an indicator of the member's chronic disease history by a third value to generate a third cost estimate, and/or multiply other factors by other values to generate other cost estimates. These conventional risk adjustment model then add the various cost estimates together to calculate a final cost estimate of the member's expected costs over the next year, or other time period.

However, cost estimates generated by such conventional linear regression-based risk adjustment models have often had a poor correlation to actual healthcare costs that members ultimately incurred. For example, many conventional risk adjustment models are less than 60% accurate at predicting which one of two given members will have higher costs over a period of time. Accordingly, the poor performance of such conventional methods of determining cost estimates may be insufficient to adequately identify high cost and/or rising risk members that may benefit the most from member outreach services.

It can also be difficult to identify when representatives should contact members to offer member outreach services. For example, even if a cost prediction indicates that a first member's healthcare costs are expected to rise by $20,000 over the next year, member outreach services may not be able to assist the first member if the first member has already been hospitalized. However, if a cost prediction for a second member indicates that the second member's healthcare costs are expected to rise by $10,000 over the next year, there may still be time for member outreach services to assist the second member before those costs are incurred, and/or to prevent those costs from being incurred. Accordingly, in this example, although the first member has a greater predicted rise in costs than the second member, the second member may be a better candidate for member outreach services because the second member's situation is more "intervenable" by member outreach services than the first member.

The systems and methods described herein can prompt member outreach services to be offered to members based on predictions generated by an ensemble of different base predictive models that are weighted based on feedback from representatives. For example, the ensemble of base predictive models can generate a set of base predictions for a member of a health plan. The base predictions can be combined into a final prediction, using weights associated with the various base predictive models. The predictions can, for example, indicate predicted costs and/or changes in costs of members over a future period of time. The predictions may also indicate predicted utilizations and/or predicted risk metrics associated with members. The predictions can thus indicate which members are high cost and/or rising risk members that should be contacted to offer member outreach services. Over time, feedback from representatives who offer member outreach services to members can be used to adjust the weights used to combine the base predictions into the final prediction. In some cases, this may cause some lower cost members to be prioritized for member outreach services over some higher cost members, if the representative feedback indicates that some lower cost members are more "intervenable" using member outreach services than some higher cost members.

Accordingly, the predictions made by the systems and methods described herein can be more accurate than conventional predictions made using linear regression methods alone. For example, test data has shown improved performance of an example of the ensemble-based model described herein, relative to previous risk models that seek to predict who will become a high-risk claimant or who is a rising risk member. For example, based on various input data types including diagnosis-only data, pharmacy-only data, diagnosis and pharmacy data, and/or a combination of diagnosis data, pharmacy data, and prior year costs, the test data indicated that the ensemble-based model described herein performed better than other risk models with respect to metrics including a percentage of cost variation explained by the model, a mean absolute error from perfect accuracy, and an area under the curve (C-statistic) indicating a probability of correctly predicting which of two people are higher risk. Based on this improved accuracy of predictions, the systems and methods described herein can better identify which members are likely to become high cost and/or rising risk members, and may therefore be better candidates for member outreach services.

As such, the ensemble-based model described herein can improve identification of members who may benefit the most from member outreach services that assist the members with finding care, arranging care, and that provide other medical and social support and education to members. Accordingly, time and computing resources associated with member outreach services can be more efficiently directed to those members who may benefit the most from those member outreach services. Additionally, attributes that lead the ensemble-based model to identify a member as a high cost or rising risk member can be identified to a representative in an outreach ticket, such that the identification of such attributes in an outreach ticket can improve efficiency of a member outreach workflow and/or reduce computing resources used by the representative. For example, rather than cold-calling the member without prior knowledge of what the member may need, or using time and computing resources to independently research the member's situation before contacting the member, a representative can use information provided directly in an outreach ticket to understand why a member may benefit from member outreach services.

FIG. 1 depicts an example of a member outreach system 100 associated with an administrator of a health plan. In some examples, the administrator can administer the health plan on behalf of a sponsor. For example, the sponsor can be an employer that offers a health plan to its employees and/or family members of the employees, and the administrator can be a third-party entity that manages the health plan for the employer. In other examples, the sponsor can be an insurance company or any other entity that offers a health plan, but uses a third-party administrator to manage administration of the health plan. In still other examples, the administrator can itself be an insurance company or other entity that directly offers a health plan.

The member outreach system 100 can be associated with member outreach services that can be provided by the administrator to members 102 of the health plan. Member outreach services may, for example, help members 102 find in-person healthcare services, help members 102 make healthcare appointments, help members 102 find transportation to and from healthcare appointments, educate members 102 about their medical conditions or medications, and/or otherwise assist members 102 in overcoming hurdles in obtaining healthcare services.

The member outreach system 100 can predict when members 102 may benefit from member outreach services. In some examples, when the member outreach system 100 predicts that a member 102 may benefit from member outreach services, the member outreach system 100 can prompt a representative 104 to attempt to contact the member 102 to offer the member outreach services. A representative 104 can be a nurse, physician, pharmacist, social worker, member outreach agent, care coordinator, or any other type of representative of the administrator or an associated entity. In other examples, when the member outreach system 100 predicts that a member 102 may benefit from member outreach services, the member outreach system 100 can automatically send notifications or other information directly to the member 102, as discussed further below. In still other examples, predictions made by the member outreach system can be used to refer members 102 to partner providers or other entities. Accordingly, such partner providers may be able to provide healthcare services directly to members 102 in addition to, or instead of, member outreach services provided by representatives 104.

The member outreach system 100 can include one or more computing devices 106, such as servers, workstations, cloud computing elements, and/or other computing devices. The computing devices 106 can have, and/or access, at least one healthcare data repository 108. The computing devices 106 can also have a prediction engine 110 and a ticket manager 112. In some examples, the ticket manager 112 may be part of the prediction engine 110. In other examples, the prediction engine 110 and the ticket manager 112 can be separate components that execute on the same or different computing devices 106. One or more healthcare data repositories 108 may also be stored on the same or different computing devices 106 than the prediction engine 110 and/or the ticket manager 112.

In some examples, representatives 104 can use computing devices 106 to access the ticket manager 112 and/or other elements of the member outreach system 110. For example, a representative 104 can use a computer, workstation, mobile device, or other type of computing device 106 to locally execute an application that interfaces with the ticket manager 112 and/or other elements of the member outreach system 110 executing on a server or other remote computing device 106. As another example, a representative 104 can use a computer, workstation, mobile device, or other type of computing device 106 to access the ticket manager 112 and/or other elements of the member outreach system 110 executing on one or more different computing devices 106 via a web browser or other user interface. In still other examples, a representative 104 may directly use the same one or more computing devices 106 that store and/or execute the healthcare data repository 108, prediction engine 110, and/or ticket manager 112.

Figure 2:
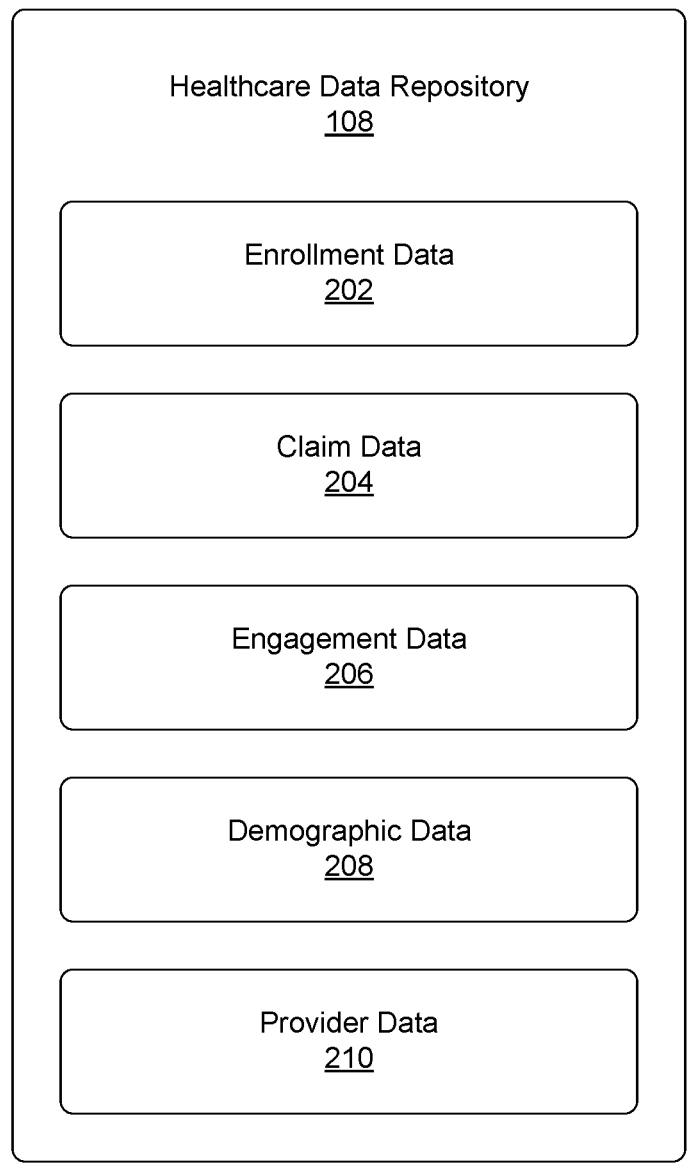
FIG. 2 depicts an example of data that can be stored in a health healthcare data repository.

FIG. 2 depicts an example of data that can be stored in a health healthcare data repository 108. A healthcare data repository 108 can be a database or other type of data repository that stores data associated with members 102 of a health plan, data about healthcare claims associated with members 102 of the health plan, data about healthcare providers, and/or other data. In some examples, a healthcare data repository 108 can use HIPAA-compliant security measures, and/or other security measures, to protect the privacy of stored information. In some examples, a healthcare data repository 108 can store enrollment data 202, claim data 204, engagement data 206, demographic data 208, provider data 210, and/or other types of data.

Enrollment data 202 can include information about members 102 that has been provided by members, sponsors, partner networks, and/or other entities. For example, enrollment data 202 can include a member's name, age, gender, ZIP code, other contact information, and/or other types of information about the member 102. In some examples, information in the enrollment data 202 may have been provided by a member 102 when the member 102 filled out enrollment paperwork online or on paper forms when the member 102 signed up for the health plan. In other examples, enrollment data 202 can be provided by a sponsor of the health plan, such as an employer that enrolls employees in a health plan and provides employee information as enrollment data 202. In still other examples, enrollment data 202 can be provided by, and/or updated by, members 102 through a health plan account website, mobile application, and/or other mechanism.

Claim data 204 can include information about insurance claims or other claims that have been submitted in association with members 102 of one or more health plans. Claims may be submitted by members 102, healthcare providers, and/or other sources. Claims may be associated with healthcare services, such as medical services, pharmaceutical services, dental services, vision care services, and/or other types of services. For example, when a member 102 obtains healthcare services from a healthcare provider, the member 102 and/or the healthcare provider may submit a claim to have some or all of the cost of the healthcare services be covered by a health plan. In some examples, claims may be submitted directly to the administrator. In other examples, claims may be submitted to insurance companies or other entities, who then provide claim data 204 to the administrator. In some examples, claim data 204 can include information from partner networks, partner providers, other administrators, and/or other entities about claims submitted against other health plans.

Data included within submitted claims, data provided in association with submitted claims, and/or data derived from submitted claims can be stored as claim data 204 within a healthcare data repository 108. For example, claim data 204 can include names, membership numbers, contact information, and/or other information about members 102 associated with submitted claims. Claim data 204 can include names, identifiers, contact information, and/or other information about healthcare providers associated with submitted claims. For instance, claim data 204 can include a national provider identification number of a healthcare provider associated with a claim. In some examples, information in claim data 204 about healthcare providers can also correspond to provider data 210 stored in the healthcare data repository 108.

In some examples, claim data 204 can include diagnosis information associated with submitted claims. For instance, diagnosis information may be included in a submitted claim using a diagnosis code, such as diagnoses codes defined in the 10$^{th}$ revision of the International Classification of Diseases, Clinical Modification (ICD-10-CM), or other types of diagnosis codes. In some examples, ICD-10-CM codes or other diagnosis codes can be categorized into diagnosis categories within claim data 204, such as Clinical Classification Software (CCS) codes used by the Agency for HealthCare Quality and Research.

In some examples, claim data 204 may also include information from pre-authorization requests that have been submitted prior to planned healthcare procedures. For instance, a pre-authorization request for a radiology procedure may be submitted by a provider to check whether a member's health plan covers that radiology procedure. In this example, information in or derived from the pre-authorization request can be added to the claim data 204 in the healthcare repository to indicate that a healthcare procedure may be planned for a member 102, even if a final claim for that procedure has not yet been received.

In some examples, claim data 204 may be received from partners of the administrator that offer services that may not be directly covered by a health plan. For example, an employer may be a sponsor that offers employees a health plan that does not directly cover fertility services. However, the administrator may partner with certain fertility service providers, and recommend such fertility service providers to members even if they are not directly covered by the members' health plan. Alternatively, the sponsor employer may offer fertility services through a partner provider as a separate benefit apart from a health plan. Accordingly, such partner providers may provide the administrator with some types of data about whether members 102 have used the partner provider's services, and such data can be stored as claim data 204 in the healthcare data repository 108 even if no official claim has been submitted in association with those services.

Engagement data 206 may include information about how members 102 have used websites, mobile applications, and/or other resources provided by the administrator. For example, the administrator may provide websites or mobile applications that allow members 102 to search for providers, contact providers, access a member portal to update enrollment data 202, and/or perform other actions associated with a health plan. The engagement data 206 may indicate whether members 102 have registered for an account to access a website and/or mobile application, what searches those members 102 have performed in the website and/or mobile application, whether members 102 clicked through on search results to view provider information and/or contact providers, whether members 102 have taken action on care recommendations provided to them through the website and/or mobile application, and/or other types of usage data or engagement data. In some examples, the engagement data 206 may also indicate locations of members 102. For example, when a member 102 uses a mobile application on smartphone, the mobile application may report location information about the smartphone, such as GPS coordinates. The mobile application can use that location information to display information about healthcare providers who are near the member's location, such as information about nearby healthcare providers that is drawn from the provider data 210 or other data sources. Location information associated with a mobile application and/or smartphone can also be stored in engagement data 206 in association with a member 102.

Demographic data 208 can include information, such as publicly available information, about people and/or environmental conditions in different geographical locations. For example, demographic data 208 can indicate, for a given ZIP code, education levels of people in the ZIP code, air pollution rates in the ZIP code, cancer rates in the ZIP code, a number of fast food restaurants in the ZIP code, and/or other types of information.

Provider data 210 can include information about healthcare providers. For example, the provider data 210 can include names of healthcare providers, names of doctors or other healthcare workers who are associated with the healthcare providers, locations of the healthcare providers, contact information for the healthcare providers, information about specialties of the healthcare providers, national provider identification numbers of the healthcare providers, and/or other information about healthcare providers.

The healthcare repository 108 can be accessible or indexed at a member level. For example, data in the healthcare repository 108 can be correlated, filtered, indexed, or searched at a member level. As a non-limiting example, for a particular member 102, information about the member 102 can be obtained from the enrollment data 202, information from claims associated with the member 102 can be obtained from the claim data 204, information about how the member 102 has used a website and/or mobile application can be obtained from the engagement data 204, and information about demographics and/or environmental conditions in the member's ZIP code can be obtained from the demographic data 208.

In some examples, the healthcare repository 108 may also, or alternately, be accessible or indexed at a provider level. For example, data in the healthcare repository 108 can be correlated, filtered, indexed, or searched at a provider level, for instance in association with one or more healthcare providers identified in provider data 210 and/or in claim data 204. As a non-limiting example, claim data 204 for claims associated with certain providers may be used to identify trends associated with individual providers, trends within one set of providers relative to other providers, geographical provider trends, and/or other provider-level data. As another non-limiting example, claim data 204 may reveal that one provider generally recommends physical therapy before scheduling a type of surgery, while another provider schedules that type of surgery without first attempting physical therapy. As yet another non-limiting example, claim data 204 may reveal local trends, for instance that providers in one locality are more likely to recommend a certain type of procedure as treatment for a particular medical condition than similar providers in a different locality.

In some examples, provider-level data can be used in the prediction engine 110 to generate predictions 114 of costs and/or visits associated with the providers. In other examples, provider-level data can also be used when representatives 104 provide member outreach services to members 102. For example, if provider-level data indicates that a first provider often charges much more for a type of procedure than a second provider, representatives 104 may recommend or suggest to members 102 that the members 102 visit the second provider.

In some examples, the healthcare repository 108 can be accessible or indexed at both the member level and the provider level. As an example, enrollment data 202 and/or claim data 204 may identify demographic information about a member 102, such as the member's age, sex, and ZIP code. Such member-specific demographic information can be referenced against claim data 204 associated with healthcare providers members 102 have visited, to determine practice patterns of the healthcare providers. Such member-level data and provider-level data may accordingly be used together in the prediction engine 110, as discussed further below.

Returning to FIG. 1, the prediction engine 110 can use data from the one or more healthcare data repositories 108 to generate predictions 114 associated with the members 102. Examples of how the prediction engine 110 can be configured to generate predictions 114 are discussed in more detail below with respect to FIG. 3 and FIG. 4.

A prediction 114 generated by the prediction engine 110 for a member 102 can indicate one or more cost estimates associated with the member 102, such as a total estimated healthcare cost, and/or a change in healthcare costs relative to previous healthcare costs, associated with the member 102 over the next year or other future time period. For example, a prediction 114 may include an indication that a member's healthcare costs are predicted to rise, or decrease, by a predicted amount over the next year.

A prediction 114 may also, or alternately, indicate one or more estimated utilizations associated with the health plan. For example, a prediction 114 can include an estimated number of visits to healthcare providers in total, and/or an estimated number of visits to providers in one or more provider categories, over the next year or other future time period. As a non-limiting example, a prediction 114 may indicate that, based on data in one or more healthcare data repositories 108, a member 102 is predicted to incur $15,000 more in healthcare costs over the next year than the previous year, and is predicted to visit healthcare providers ten times over the next year, including three visits to emergency rooms, four visits to a primary care physician, two visits to a cardiologist, and one visit to a chiropractor.

A prediction 114 may also, or alternately, indicate one or more estimated risk metrics associated with a member 102. For example, a prediction 114 can indicate predicted risk metric values such as a predicted risk of hospitalization, a predicted risk of readmission to a hospital, a predicted mortality rate, predicted suffering or pain levels, a predicted risk of pharmaceutical advancement to more expensive medications and/or to medications with increased levels of side effects, and/or other types of predicted risk metrics.

In some examples, member outreach services can be offered to members 102 based on predicted risk metrics of the members 102, and/or comparisons between predicted risk metrics for different members 102. For example, predictions 114 may indicate that a pain level of a first member 102 is expected to be higher than a pain level of a second member 102, based on claim data 204 indicating that the first member 102 has been diagnosed with a disease that is generally more painful than a disease with which the second member 102 has been diagnosed. In this example, the first member 102 may in some cases be prioritized for member outreach services over the second member 102, as the member outreach services may help reduce the higher predicted pain levels of the first member 102. As another example a prediction 114 may indicate that a suffering level and/or mortality risk for a particular member 102 is expected to increase over the next two months. Accordingly, the member 102 can be prioritized for member outreach services that may help reduce, or lessen the increase in, the member's suffering level or mortality risk.

In some example, the various types of information associated with a member 102 in the healthcare data repositories 108 may provide more complete information about a member 102 for the prediction engine 110 than could be provided by claim data 204 alone. For instance, engagement data 206 may indicate that a member 102 was using a mobile application to search for and contact podiatrists before claim data 204 indicates that foot care claims for the member 102 have been submitted. The engagement data 206 may therefore be used by the prediction engine 110 to predict that the member's healthcare costs may be expected to rise over the next month due to possible upcoming foot care services, even if claim data 204 does not yet indicate that foot care services have been provided to the member 102.

Provider-level data from the healthcare data repositories 108 can be used by the prediction engine 110 to make predictions 114 associated with members 102. For example, enrollment data 202 engagement data 206, and/or provider data 210 may indicate that a member 102 is located in a geographical area where a provider-level data indicates that an expensive procedure is used more often to treat a certain condition than in other locations. As another example, past claim data 204 and/or provider data 210 may indicate that a specific provider, that engagement data 206 indicates a member 102 has searched for, routinely uses an expensive procedure more often than other nearby providers. In these examples, the prediction engine 110 may predict that the member's costs may be expected to rise due to a relatively high chance of the expensive procedure being performed.

Overall, machine learning and/or other artificial intelligence in the prediction engine 110 can analyze data in one or more healthcare data repositories 108, at the member-level and/or the provider-level, to generate predictions 114 based on multiple factors and/or interactions between multiple factors. For example, various factors from enrollment data 202, claim data 204, engagement data 206, and/or demographic data 208 may indicate that people in relatively-low income ZIP codes who take insulin to treat diabetes have a spike in emergency room visits during the last week of each month, possibly because such people have relatively little money left from a first-of-the month paycheck and don't have sufficient food to prevent insulin dosages leading to low blood sugar. The predictive engine 110 can take such factors, and/or interactions between such factors, when generating predictions 114 of costs, health plan utilizations, risk metrics, and/or other values. As will be discussed below with respect to FIG. 3, the prediction engine 110 can include multiple base predictive models 304 that can take various factors from one or more healthcare data repositories 108 into account when generating base predictions 306. The base predictions 306 from multiple base predictive models 304 can be combined into a final prediction 114.

Based on predictions 114 generated by the prediction engine 110, the ticket manager 112 can be configured to generate outreach tickets 116 for representatives 104. The outreach tickets 116 can be viewable and/or accessible via computing devices 106 used by the representatives 104. The representatives 104 can at least attempt to contact members 102 identified by outreach tickets 116 to offer member outreach services to the members 102. The representatives 104 can also use computing devices 106 to provide ticket feedback 118 to the ticket manager 112 about outreach tickets 116 and/or corresponding members 102. As will be discussed further below, the prediction engine 110 can use ticket feedback 118 provided by representatives 104 to adjust how the prediction engine 110 generates subsequent predictions 114. In some examples, the computing devices 106 may also, or alternately, provide automated notifications 120 to members 102 in response to generated predictions 114.

In some examples, the ticket manager 112 can generate outreach tickets 116 based on part on cost estimates, utilization metrics, risk metrics, and/or other data in predictions 114 generated by the prediction engine 110. For example, a prediction 114 may indicate that a member's total costs are predicted to be over $50,000, or another threshold value, over the next year, and thus indicate that the member 102 is predicted to be a "high cost" member 102. As another example, a prediction 114 may indicate that a member's healthcare costs are predicted rise by over $1,000, or another threshold value, over the next month relative to the previous month, and thus indicate that the member 102 is predicted to be a "rising risk" member 102. A member 102 may also, or alternately, be considered to be a "rising risk" member 102 if risk metrics in a prediction 114 indicates that the member 102 is predicted to utilize or visit healthcare providers in a future time period more often than the member 102 has in the past, that the member's risk of admission or readmission to a hospital or other healthcare facility is precited to increase, that the member's suffering levels or mortality risks are expected to increase relative to previous values, that the pharmaceutical usage is predicted to advance to more expensive medications and/or to medications with increased side effects, and/or that the member's risk in any other category is predicted to increase during a future time period.

In these examples, the ticket manager 112 may generate an outreach ticket 116 associated with the member 102 due to the total costs, or one or more predicted rises in costs, utilizations, and/or risk metrics, exceeding a threshold amount. Based on the outreach ticket 116, member outreach services may be able to proactively assist the member 102 to obtain healthcare services and/or otherwise manage the healthcare issues associated with the predicted costs, utilizations, or risk metrics. For instance, member outreach services may be able to assist the member 102 with proactively seeking medical care, before a condition worsens and more costly healthcare services may be needed to manage the condition. Member outreach services may therefore proactively improve the health of the member 102, reduce the healthcare costs ultimately incurred by the member 102, reduce a number of utilizations associated with the member 102, and/or reduce risk metrics associated with the member 102. Accordingly, in some examples, member outreach services may cause healthcare costs incurred by a member 102 over a period of time to be lower than cost estimates in a prediction 114 for that period of time.

An outreach ticket 116 can identify a corresponding member 102, for example as by including the member's name, contact information, and/or other demographic information. The outreach ticket 116 may also indicate one or more reasons why the member 102 may benefit from member outreach services, based on information in a final prediction 114 and/or base predictions 306. For example, key variables from the healthcare data repository 108 that most influenced the final prediction 114 and/or base predictions 306 can be identified and flagged within an outreach ticket 116. In some examples, a Local Interpretable Model-Agnostic Explanations (LIME) method can be used to identify the variables that most influenced a prediction 114 or its component base predictions 306. For example, a LIME analysis may indicate that a new cancer diagnosis or a change in prescribed medications was one of the primary reasons that caused the prediction engine 110 to generate a prediction 114 indicating that a member 102 is expected to have a rise in costs, a rise in utilizations, and/or increased risk metrics over an upcoming period of time, while a recent procedure for a flu shot is not a key variable that is associated with the predicted rise in costs, utilizations, or risk metrics. The ticket manager 112 can generate an outreach ticket 116 that includes indicators of the identified key variables. For instance, in some examples, the ticket manager 112 can generate an outreach ticket 116 by filling in blanks of a template with language associated with the identified key variables, such as the new cancer diagnosis or the change in prescribed medications, to indicate to a representative 104 why the corresponding member 102 may benefit from member outreach services.

As another example, if claim data 204 indicates that the member 102 has been diagnosed with diabetes, but has not recently filled a prescription for insulin, the prediction engine 110 may generate a prediction indicating that the member's costs are predicted to rise due to increased visits to a diabetes specialist to manage conditions resulting from missed medications. In this example, the ticket manager 112 may generate an outreach ticket 116 indicating to a representative 104 that the member 102 may need assistance with insulin medications or other issues associated with diabetes.

In some examples, the ticket manager 112 may use data in a prediction 114, such as cost predictions, predicted total utilizations across all types of providers, predicted utilizations of one or more specific providers or types of providers, and/or predicted risk metrics to select corresponding words, phrases, or values for variables in templates for outreach tickets 116. For example, the ticket manager 112 may have one or more templates for outreach tickets 116. A template may or may not have some predefined language, and may include blank spaces where words or phrases can be inserted, variable fields where values can be entered or selected, or other portions that can be otherwise changed based on a prediction 114. For example, the ticket manager 112 may select words, phrases, or other values for corresponding elements of a template based on key variables of predictions 114 generated by the prediction engine 110.

A generated outreach ticket 116 may assist a representative 104 in understanding what types of member outreach services should be offered to a member 102. For example, if key variables from predictions 114 indicated that a first member 102 has been diagnosed with a foot problem and also has been diagnosed with diabetes, an outreach ticket 116 may identify those diagnoses. A representative 104 may accordingly understand from the outreach ticket 116 that the first member 102 may need assistance with insulin medications or other diabetes-related issues. However, if a prediction 114 for a second member 102 indicates a diagnosis of a similar foot issue but also indicates that the second member 102 has been visiting a sports therapist, the member's foot issue may have occurred because the second member 102 is a runner. In this example, a representative 104 may understand from a corresponding outreach ticket 116 that the second member 102 may need a different type of patient outreach services than the first member 102 who has diabetes. As will be discussed further below, ticket feedback 118 can be received from a representative 104 about how "interpretable" the information in the outreach ticket 116 was to the representative 104, such a score indicating whether the outreach ticket 116 expressed understandable and/or useful information to the representative 104.

The ticket manager 112 can provide the outreach tickets 116 to representatives 104. In some examples, the ticket manager 112 can add a generated outreach ticket 116 to a queue of outreach tickets 116 available to representatives 104. For instance, a representative 104 may use a user interface of the ticket manager 112, or other application executing on a computing device 106, to view and/or select outreach tickets 116 from the queue of outreach tickets 116. In other examples, the ticket manager 112 can send a generated outreach ticket 116 to a representative 104 via an email, text message, or other type of electronic notification, and/or otherwise provide the outreach ticket 116 to a representative 104.

In some examples, the outreach tickets 116 may be associated with priority levels, and the ticket manager 112 can arrange, sort, and/or filter outreach tickets 116 in the queue based on priority levels of the outreach tickets 116. For instance, the ticket manager 112 can arrange a queue such that more urgent outreach tickets 116 are prioritized over, and/or placed closer to the front or to the top of the queue than, less urgent outreach tickets 116. As will be discussed further below, a priority level of an outreach ticket 116 can be based at least in part on cost estimates, utilization estimates, risk metric estimates, or other data in an associated prediction 114. For example, a first outreach ticket 116 associated with a first prediction 114 indicating that a first member's costs are expected to rise by $15,000 may be a higher priority than a second outreach ticket 116 associated with a second prediction 114 indicating that a second member's costs are expected to rise by $10,000.

However, in some examples, a priority level of an outreach ticket 116 can also be based, at least in part, on ticket feedback 118 from representatives 104. The ticket feedback 118 can indicate indicating how "interpretable" previous similar outreach tickets 116 were to the representatives 104, based on how well the representatives 104 subjectively felt that the previous outreach tickets 116 expressed information about why a member 102 was to be contacted. The ticket feedback 118 can also, or alternately, indicate how "intervenable" members 102 identified by previous similar outreach tickets 116 were, based on subjective input from representatives 104 about whether those members 102 were good candidates for member outreach services. For instance, in the example above, if previous ticket feedback 118 from representatives 104 has indicated that members 102 similar to the second member 102 are more "intervenable" via member outreach services than members 102 similar to the first member 102, the second outreach ticket 116 may be prioritized above the first outreach ticket 116 even though the first outreach ticket 116 is associated with a higher predicted rise in costs.

Based on an outreach ticket 116 that identifies a member 102, a representative 104 can at least attempt to contact the member 102 to offer and/or provide member outreach services to the member 102. For example, the representative 104 can place a phone call to a phone number of the member 102, send a text message to the phone number of the member 102, send an email to an email address of the member 102, initiate a video chat with the member 102, and/or otherwise at least attempt to contact the member 102 to provide member outreach services to the member 102.

In some examples, the computing devices 106 can alternately, or additionally, attempt to contact a member 102 identified by a prediction 114 and/or an outreach ticket 116 via an automated notification 120. For example, the computing devices 106 can be configured to send an email to an email address of the member 102, send a text message to a phone number of the member 102, make a phone call to a phone number of the member 102 to play a prerecorded audio message for the member 102 via the phone call, display a flagged notification in a member portal accessible via a website or mobile application, display a notification on a smartphone via a mobile application, and/or attempt to contact the member 102 using any other automated communication mechanism. An automated notification 120 can, based on a prediction 114, indicate to the member 102 why the member 102 is being contacted. For example, an automated notification 120 can be an automated email that reminds a member 102 to take a medication and/or that provides medication instructions.

In some examples, a healthcare data repository 108, or other information about members 102 that is available to the computing devices 106, may indicate communication preferences of members 102. For example, communication preferences of a member 102 may indicate that the member 102 prefers phone calls over email communications. In this example, the computing devices 106 may follow the communication preferences of the member 102 by providing an outreach ticket 116 to a representative 104, so that the representative 104 can place a phone call to the member 102. If the communication preferences of the member 102 instead indicate that the member 102 prefers email communications over phone calls, the computing devices 106 may instead attempt to contact the member 102 using an emailed automated notification 120 instead of providing an outreach ticket 116 to a representative 104. In some examples, communication preferences of a member 102 may be based on enrollment data 202, such as from preference information indicated by the member 102 on a health plan enrollment form. In other examples, the computing devices 106 can infer or derive communication preferences of a member 102 based on engagement data 206 or other data about interactions with the member 102 over time. For instance, if a member 102 answers phone calls from administrator personnel more often than the member 102 responds to emails from the administrator, the computing devices 106 can infer that the member 102 prefers to communicate via phone calls and indicate that inferred preference in data about communication preferences of the member 102.

In some examples, the computing devices 106 may override communication preferences of a member 102. For example, if a prediction 114 and/or outreach ticket 116 is generated with a priority level above a certain threshold, for instance if the member 102 is predicted to incur a sudden rise in costs over a short period of time, the ticket manager 112 may provide an outreach ticket 116 to a representative 104. The outreach ticket 116 may instruct the representative 104 to call the member 102 to address conditions associated with the predicted sudden rise in costs, even if communication preferences of the member 102 indicate that the member 102 prefers email communications.

When the computing devices 106 provide an outreach ticket 116 for a member 102 to a representative 104, the representative 104 may at least attempt to contact the member 102 to provide member outreach services, as discussed above. The representative can also return ticket feedback 118 associated with the outreach ticket 116 to the computing devices 106. The ticket feedback 118 can include subjective feedback from the representative 104 about an outreach ticket 116. In some examples, the ticket manager 112 can provide a survey, form, user interface, and/or other mechanisms that representatives 104 can use to provide ticket feedback 118.

In some examples, ticket feedback 118 may indicate a score, based on subjective input from a representative 104, of how "intervenable" a member 102 was via member outreach services. For example, if a representative 104 could not reach a member 102 to offer member outreach services because the member 102 had already been hospitalized for a medical condition, the representative 104 may provide ticket feedback 118 with a score indicating that the member 102 was a relatively poor candidate for member outreach services because no intervention prior to hospitalization was possible. Similarly, if a representative 104 determines that a member 102 has a terminal disease for which little meaningful intervention is possible, the representative 104 may also provide ticket feedback 118 with a score indicating that the member 102 was a relatively poor candidate for member outreach services. However, if a representative 104 was able to successfully contact a member 102, and was able provide assistance to the member 102 that the representative 104 felt was beneficial, the representative 104 may provide ticket feedback 118 with a score indicating that the member 102 was a relatively good candidate for member outreach services. For instance, if an outreach ticket 116 indicates that a member 102 was recently diagnosed with asthma, the representative 104 may be able to educate the member 102 about how to use an inhaler and thereby reduce the risk of the member 102 visiting an emergency room due to the member's asthma.

In some examples, ticket feedback 118 may also, or alternately, indicate a score, based on subjective input from a representative 104, of how "interpretable" an outreach ticket 116 was to the representative 104. For example, if an outreach ticket 116 identifies a member 102 but does not indicate why that member 102 is being referred for member outreach services, a representative 104 may not understand from the outreach ticket 116 why the member 102 is to be contacted. The representative 104 may need to call the member 102 without understanding the member's situation, which may impact the quality or types of member outreach services provided to the member 102. In this case, the representative 104 may provide ticket feedback 118 indicating that the outreach ticket 116 itself was unclear and/or unhelpful to the representative 104.

In some examples, ticket feedback 118 can be based on Likert scale assessments by a representative 104 of one or more aspects of an outreach ticket 116. As an example, a representative 104 can provide a rating on a scale of 0 to 5, or any other scale, for categories such as "intervenability," "interpretability," and/or other categories associated with an outreach ticket 116. For instance, the representative 104 can provide an intervenability rating on a 0 to 5 scale based on whether the representative 104 felt that the member 102 identified by the outreach ticket 116 was a suitable candidate for member outreach services, and can also provide an interpretability rating on a 0 to 5 scale based on whether the representative 104 felt that the outreach ticket 116 sufficiently explained a health issue or rise in costs associated with the member 102 that could be addressed using member outreach services. In some examples, scores in different categories can be summed together, or otherwise combined, into a total score for the ticket feedback 118. For example, if a representative 104 provides an intervenability score of "3" and an interpretability score of "4," the ticket feedback 118 may indicate a total score of "7" for an outreach ticket 116.

In some examples, the ticket manager 112 can provide a user interface for representatives 104 to enter scores for ticket feedback. For example, the user interface can provide a user interface with sliders, radio buttons, dropdown menus, freeform data entry fields, and/or other user interface elements that representatives 104 can use to enter intervenability scores, interpretability scores, and/or other types of ticket feedback 118 associated with outreach tickets 116.

Ticket feedback 118, for example as submitted to the ticket manager 112, can be provided to, and/or shared with, the prediction engine 110. The prediction engine 110 can use the ticket feedback 118 to adjust weights used within the prediction engine 110 to combine base predictions into a final prediction 114, as discussed further below with respect to FIG. 3 and FIG. 4.

In some examples, the member outreach system 100 can also, or alternatively, use a prediction 114 to determine if or when a member 102 is suitable for intervention by a healthcare provider that partners with the administrator. For example, in addition to, or instead of, providing an outreach ticket 116 to a representative, the member outreach system 100 may generate a referral for a partner provider, such that the partner provider can contact the member 102 to directly offer corresponding healthcare services to the member 102. In this example, the prediction engine 110 can use other types of feedback associated with the partner provider and/or the member, in addition to or instead of ticket feedback 118, to adjust predictions 114 or how predictions 114 are generated. For example, if a partner provider indicates that it provided treatment to a member 104, the prediction engine 110 can determine if that treatment ultimately reduces actual healthcare costs incurred by the member 102, reduces predicted healthcare costs during future time periods, and/or improves the member's health over time. If such actual or predicted cost reductions and/or health improvements do occur, the prediction engine 110 can use machine learning and/or other artificial intelligence techniques to learn that similar members 102 should be referred to the partner provider in the future.

Figure 3:
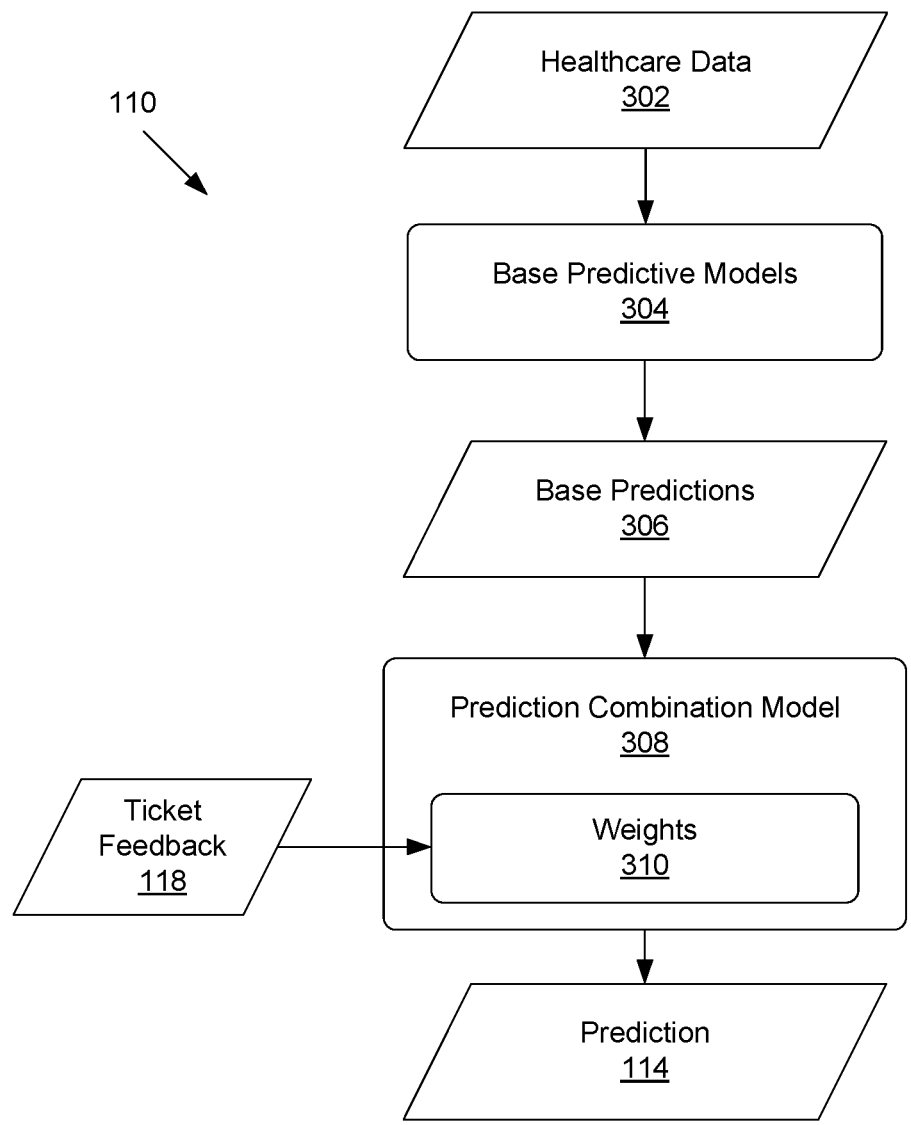
FIG. 3 depicts an example of a prediction engine.

FIG. 3 depicts an example of the prediction engine 110. The prediction engine 110 can include an ensemble of multiple base predictive models 304. The base predictive models 304 can be configured to, based at least in part on healthcare data 302 from one or more healthcare data repositories 108, generate base predictions 306 associated with members 102 of a health plan. In some examples, the healthcare data 302 used by the base predictive models 304 can include enrollment data 202, claim data 204, engagement data 206, demographic data 208, provider data 210, and/or other types of data at a member level and/or at a provider level, as discussed above. Similar to the final predictions 114 output by the prediction engine 110, an individual base prediction 306 produced by an individual base model 304 can include an estimate of costs that a member 102 will incur over a period of time, and/or an estimated change in such costs relative to previous costs incurred by the member 102. A base prediction 306 may also include estimated utilization data, such as predictions of how many times a member 102 will visit providers in one or more categories, and/or in total, over a period of time.

The base predictive models 304 can be machine learning models, artificial intelligence models, and/or other types of predictive models. For example, the base predictive models 304 can include, or be based on, regularized linear algorithms, Gradient Boosted Machines (GBMs), Random Forest algorithms, deep learning algorithms, recurrent neural networks, other types of neural networks, nearest-neighbor algorithms, support-vector networks, linear regression, logistic regression, other types of regression analysis, decision trees, and/or other types of artificial intelligence or machine learning frameworks.

As an example, a base predictive model 304 can be a tree-based learning model that generates trees with different branches associated with different factors. For instance, a tree-based leaning model can generate a tree with a branch for whether a member 102 has a diabetes, a subsequent branch for whether the member 102 is on insulin, a subsequent branch for whether the member 102 is in a low-income ZIP code, and a subsequent branch for whether it is the last week of the month. If data for a member 102 indicates that the answer is "yes" for all of these branches, the tree may indicate a base prediction 306 at an ending node of the branches with predicted costs, utilizations, and/or risk metrics for members 102 who meet that criteria. For example, as discussed above, members 102 who meet the criteria of this example have increased chances of visiting emergency rooms.

Figure 4:
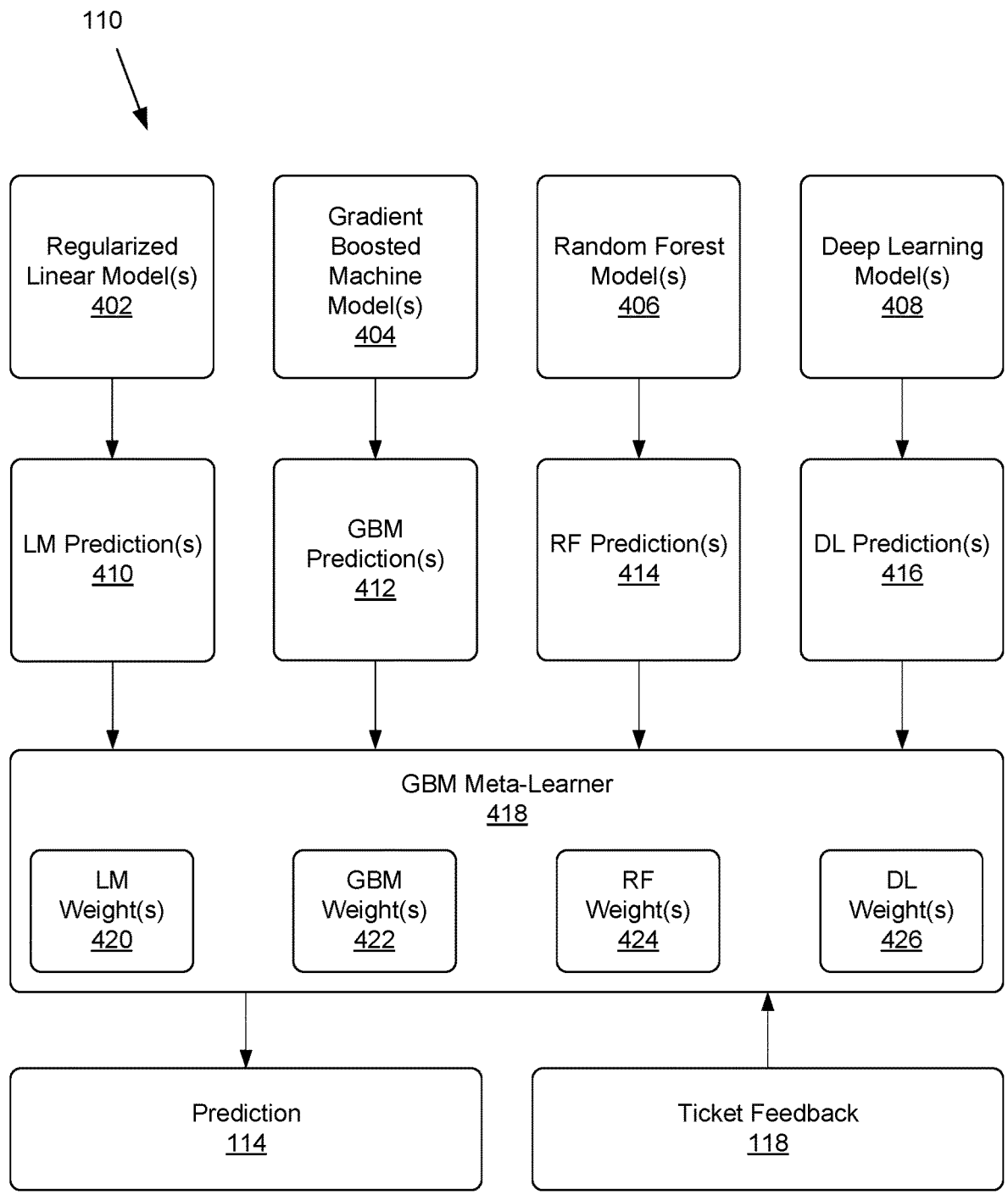
FIG. 4 depicts a non-limiting example of a prediction engine in which an ensemble of base predictive models includes instances of four types of base predictive models.

In some examples, the ensemble of base predictive models 304 can include at least two types of predictive models. For example, FIG. 4, discussed further below, depicts a non-limiting example in which the prediction engine 110 includes four types of base predictive models 304, including regularized linear models 402, GBM models 404, Random Forest models 406, and deep learning models 408. However, although four types of base predictive models 304 are shown in the example of FIG. 4, the prediction engine 110 may include different types of base predictive models 304 than are shown in FIG. 4. Additionally, although FIG. 4 shows an example with four different types of base predictive models 304, the prediction engine 110 can have two different types of base predictive models 304, three different types of base predictive models 304, four different types of base predictive models 304, five different types of base predictive models 304, or any other number of different types of base predictive models 304.

Different types of predictive models may have different strengths and weaknesses, such that some types of predictive models may be better suited to make base predictions 306 about certain types of situations than other types of predictive models. Accordingly, even if a particular type of predictive model is not well-suited to make base predictions 306 for a certain type of situation associated with a member 102, one or more other types of predictive models in the ensemble may be better suited to make base predictions 306 for that type of situation. As will be discussed below, base predictions 306 from multiple base predictive models 304 can be combined together into a final prediction 114. Accordingly, even if individual base predictive models 304 are relatively imperfect, the combined final prediction 114 can more closely approximate actual results than the individual base predictions 304 taken in isolation.

At least some of the base predictive models 304 can be machine learning or artificial intelligence models that can be trained based on historical data in the healthcare data 302. For example, a base predictive model 304 can be trained to identify which features within historical healthcare data 302 associated with a member 102 are predictors of past healthcare costs incurred by that member 102, past visits to healthcare providers by that member 102 and/or past risk metrics associated with the member 102. When such base predictive models 304 have been trained, the base predictive models 304 can use current healthcare data 302 corresponding to the identified features to generate base predictions 306 of future costs, future utilizations, and/or future risk metrics associated with members 102.

The ensemble of base predictive models 304 may include one or more instances of each type of predictive model present in the ensemble. For example, the ensemble of base predictive models 304 can include a first set of instances of a first type of predictive model, and also include a second set of instances of a second type of predictive model. In some examples, each instance of a base predictive model 304 can be trained on a random subset of the healthcare data 302. Accordingly, one instance of a base predictive model 304 may be trained on a different random subset of the healthcare data 302 than a different instance of a base predictive model 304.

The prediction engine 110 can also have a prediction combination model 308. The prediction combination model 308 can be configured to combine a set of base predictions 306, generated by multiple base predictive models 304, into a final prediction 114. The prediction combination model 308 can, at least in part, use weights 310 associated with different types of base predictive models 304 and/or individual instances of base predictive models 304 to combine corresponding base predictions 306 into a final prediction 114. For example, if one base prediction 306 predicts that a member's costs will rise by $10,000 and another base prediction 306 predicts that the same member's costs will rise by $20,000, the prediction combination model 308 may combine the two base predictions into a prediction that the member's costs will rise by $15,000, if the base predictive models 304 that made the base predictions 306 are weighted equally. However, weights 310 associated with different base predictive models 304 may not be equal, and numerous base predictions 306 generated by numerous base predictive models 304 with varying weights 310 can be used to generate the final prediction 114.

The prediction combination model 308 can be a machine learning model, artificial intelligence model, or other type of predictive model. In some examples, the prediction combination model 308 may be referred to as a "meta-earner" or a "super learner." For instance, in some examples, the prediction combination model 308 can use gradient boosting meta-learning and/or a stacking method to determine the weights 310 to use when combining base predictions 306 into a final cost prediction 114.

In some examples, after base predictive models 304 have been trained on random samples of historical healthcare data 302, the trained base predictive models 304 can generate base predictions 306 on remaining samples of the historical healthcare data 302. Such base cost predictions 306 can be evaluated using an area under a curve statistic, known as a C-statistic, which indicates a probability of correctly predicting which of two members 102 are "high cost" members 102 with healthcare costs above a threshold value. C-statistics associated with different instances of base predictive models 304 can accordingly indicate relative performances of the different instances of the base predictive models 304, and in some examples can be used to determine corresponding weights 310 to select for the different instances of the base predictive models 304. Accordingly, in some examples, a base predictive model 304 can be trained until its C-statistic meets a threshold value. In some examples, base predictive models 304 can also be subject to regularization, such as elastic net regularization, to prevent the base predictive models 304 from overfitting their base predictions 306.

Each instance of base predictive model 304 can also be assigned a corresponding weight 310 in the prediction combination model 308. In some examples, the weights 310 for different base predictive model 304 can initially be equal, or be set to a predefined starting value. However, thereafter the prediction combination model 308 can use ticket feedback 118 provided by representatives 104 to continually or periodically adjust the weights 310 associated with different base predictive models 304. In some examples, the prediction combination model 308 may adjust weights 310 for different base predictive models 304 until predictions 114 generated using a weighted average of base predictions 306 maximizes a C-statistic in one or more cross-validation samples from training data.

As an example, the prediction engine 110 may generate a set of predictions 114 for a set of members 102, and the ticket manager 112 can generate corresponding outreach tickets 116 for the members 102 that are prioritized in a queue based on which members 102 are predicted to have the highest rise in costs. However, if ticket feedback 118 indicates that the member 102 associated with the highest priority outreach ticket 116 was not as intervenable, and/or the outreach ticket 116 was not as interpretable, than a lower-priority outreach ticket 116, the prediction engine 110 can adjust the weights 310 so that base predictions 306 from base predictive models 304 that indicated the member 102 was a high priority are down-weighted in the future.

In some examples, a loss function in the prediction combination model 308 can be adjusted to down-weight base predictive models 304 that were associated with lower ticket feedback 118 on a Likert scale or other scale, and up-weight base predictive models 304 that were associated with higher ticket feedback 118 on a Likert scale or other scale. An example of adjusting weights 310 based on ticket feedback 118 is discussed further below with respect to FIG. 5.

In some examples, the prediction engine 110 can also use other types of feedback to adjust how base predictions 306 and/or final predictions 114 are generated. For example, if a prediction 114 indicates that a member's healthcare costs are expected to rise due a new diagnosis, the prediction engine 110 can use claims data 206 to determine whether claims associated with that diagnosis are ultimately received. In some examples, the lack of later-submitted claims associated with a diagnosis can be an indication that member outreach services have been successful. As another example, the prediction engine 110 or the ticket manager 112 can track whether outreach tickets 116 are transferred between representatives 104. For instance, if an outreach ticket 116 is provided to a nurse, but the nurse determines that the outreach ticket 116 would be better handled by a pharmacist due to a medication issue and transfers the outreach ticket 116 to the pharmacist, the prediction engine 110 may use transfer data to increase the chances of similar outreach tickets 116 indicating medication issues and/or being directed to pharmacists in the future.

As noted above, FIG. 4 depicts a non-limiting example of a prediction engine 110 in which the ensemble of base predictive models 304 includes instances of four types of base predictive models 304, including regularized linear models 402, Gradient Boosted Machine (GBM) models 404, Random Forest models 406, and deep learning models 408. However, the example of FIG. 4 is not intended to be limiting, as the prediction engine 110 may include different types of predictive models than are shown in FIG. 4, and/or can include fewer, or more, than four types of base predictive models 304.

A regularized linear model 402 can be a base predictive model 304 that outputs a linear model prediction 410. A linear model prediction 410 can be a base prediction 306 of costs, utilization, risk metrics, and/or other information about a member 102. A regularized linear model 402 can be based on elastic net regularization, which seeks to minimize a penalty function over a grid of values for a regularization parameter, $\lambda$. Such regularization can avoid overfitting to noise. The regularization parameter, $\lambda$, can control the strength of a balancing parameter, $\alpha$, between lasso regression and ridge regression. In some examples, the lasso regression can be L1 regularization, which selects one correlated covariate and removes other covariates from the equation. Additionally, in some examples, the ridge regression can be L2 regularization, which shrinks coefficients of correlated covariates towards each other.

By way of a non-limiting example, for a logistic regression, a regularized linear model 402 can seek to minimize the negative binomial log-likelihood expressed in the following equation (Equation 1):

$$-\left[\frac{1}{N}\sum_{i=1}^{N}y_i \cdot (\beta_0 + x_i^T\beta) - \log(1 + e^{(\beta_0 + x_i^T\beta)}) + \lambda\left[\frac{(1-\alpha)\|\beta\|_2^2}{2} + \alpha\|\beta\|_1\right]\right]. \quad (Eq. 1)$$

In this example, regularization algorithm can perform coordinate descent on a quadratic approximation to the log-likelihood. Generalized linear modeling estimators can be trained on healthcare data 302 in the prediction engine 110 to find an optimal $\lambda$ value using Equation 1, at each $\alpha$ value, across internal cross-validations on a training dataset from the healthcare data 302. In particular, a first portion of Equation 1 (ahead of the $\lambda$ value) can determine x values that are most predictive. For example, a cancer diagnosis can be highly predictive of future costs, while a diagnosis of an eyelid flutter may not be highly predictive of future costs. As another example, an orthopedic surgery diagnosis can indicate that a member's condition may be "intervenable" through member outreach services, while an eyelid flutter diagnosis may not be "intervenable" through member outreach services. The second portion of Equation 1 (multiplied by the $\lambda$ value) can assist with pulling out noise in the data. The $\lambda$ value can be determined through machine learning to balance the two portions of the equation.

A GBM model 404 can be a base predictive model 304 that outputs a GBM prediction 412. A GBM prediction 412 can be a base prediction 306 of costs, utilization, risk metrics, and/or other information about a member 102.

GBM models 404 can develop regression trees. A GBM model 404 can be an ensemble learning algorithm that sequentially builds classification trees on features of derivation datasets, such as datasets from healthcare data 302. For example, regression trees can be developed in a GBM model 404 by sequentially selecting covariates to parse each derivation dataset into subsets with high between-group and low-within-group variance in future predicted annualized cost. Gradient boosting can seek to improve the choice of covariates and their combinations over time to minimize error between observed and predicted outcome rates in each terminal node, while repeatedly sampling from the underlying data to prevent overfitting.

In some examples, a GBM model 404 can generate a first tree based on a random sample of healthcare data 302, and then generate subsequent trees based in part on previous trees. For example, a second tree may be based on different random sample than the first tree, and the GBM model 404 can determine if predictions of the first tree or the second tree are more accurate, and adjust trees accordingly. As such, the GBM model 404 can generate trees by learning from preceding trees.

In some examples, a GBM model 404 can follow Equations 2 through 7, presented below, to build k regression trees with incremental boosts of the function f over M iterations:

Initialize $f_{k0}=0, k=1,2,\ldots,K.$ (Eq. 2)

For $m=1$ to $M$, compute the gradient $$p_k(x) = \frac{e^{f_k(x)}}{\sum_{i=1}^{K} e^{f_i(x)}}$$

for all $k=1,2,\ldots,K.$ (Eq. 3)

For $k=1$ to $K$, fit a tree to targets $r_{ikm}=y_{ik}-p_k(x_i)$, for $i=1,2,\ldots,N$, producing terminal regions $R_{jkm}$, $1,2,\ldots,J_m.$ (Eq. 4)

Calculate the step $$\gamma_{jkm} = \frac{K-1}{K} \frac{\sum_{x_i \in R_{jkm}} (r_{ikm})}{\sum_{x_i \in R_{jkm}} |r_{ikm}|(1-|r_{ikm}|)},$$

$j=1,2,\ldots,J_m.$  (Eq. 5)

Update the function $f_{km}(x)=f_{k,m-1}(x)+\Sigma_{j=1}^{J_m}\gamma_{jkm}I$
$(x\in R_{jkm})$.  (Eq. 6)

Output $\hat{f}_k(x)=f_{kM}(x)$.  (Eq. 7)

In some situations, a GBM model 404 can be tuned, and/or can be sensitive to hyperparameter choices. Accordingly, some hyperparameters can be varied across broad ranges when multiple GBM models 404 are trained. In some examples, GBM estimators can be trained with common values of a learning rate, a maximum tree depth, and a column sample rate.

The learning rate, or shrinkage, can control a weighted average prediction of the trees, and can refer to a rate (for example ranging from 0 to 1) at which the GBM models 404 change parameters in response to error (i.e., learn) when building an estimator. Lower learning rate values may enable slower learning, but may use more trees to achieve a level of fit than would be used with a higher learning rate. In some examples, lower learning rates can also help to avoid overfitting, even if the lower learning rates may be more computationally expensive.

The maximum tree depth can refer to a number of layers of the tree, and thus can control how many splits can occur to separate a population into subpopulations. For example, in some algorithms, a tree may no longer split if either a maximum depth is reached, or a minimum improvement in prediction (relative improvement in squared error reduction for a split>$1^{-5}$) is not satisfied. In some situations, deeper trees may provide more accuracy on a derivation dataset, but may also lead to overfitting.

The sample rate can refer to a fraction of the data sampled among columns of the data for each tree, which can help improve sampling accuracy. In some examples, the sample rate can be expressed on a 0 to 1 scale, such that, for instance, 0.7 refers to 70% of the data sampled. On this scale, values of the sampling rate that are less than 1 may help improve generalization by preventing overfitting. In some examples, stochastic gradient boosting can be used, such that to fit each GBM estimator, in each learning iteration a subsample of training data can be drawn at random without replacement.

A Random Forest model 406 can be a base predictive model 304 that outputs a Random Forest prediction 414. A Random Forest prediction 414 can be a base prediction 306 of costs, utilization, risk metrics, and/or other information about a member 102.

Similar to GBM models 404, Random Forest models 406 can also be associated with regression trees. In particular, Random Forest models 406 can use a broad range of hyperparameter starting values entered into a random grid search. A tree learning algorithm can apply a modified version of bootstrap aggregating (bagging), in which the tree learning algorithm selects, at each candidate split in tree learning process, a random subset of covariates to build and train the tree (feature bagging). Trees can be trained in parallel and split, until either a maximum depth is reached or a minimum improvement in prediction (such as a relative improvement in squared error reduction for a split>$1^{-5}$) is not satisfied. Forests can be fit with varied values of a maximum tree depth and column sampling rates.

As an example, a Random Forest algorithm may generate trees based which factors or variables are most predictive of actual results. For instance, a Random Forest algorithm may determine from healthcare data 302 that age is the most important predictor of hospitalizations, and that high blood pressure diagnoses are the second-most important predictor of hospitalizations. In some examples, a Random Forest model 406 may generate numerous trees based on different random subsets of data, and generate a final tree by averaging those trees to avoid overfitting.

In some examples, Random Forest models 406 may use greater maximum tree depth values, and sample from a smaller number of covariates in each tree, than GBM models 404. In some cases, the greater depth of Random Forest models 406 may cause the Random Forest models 406 to be more efficient on longer datasets, while GBM models 404 may be more efficient on wider datasets. In the Random Forest models 406, overfitting can be reduced by randomizing tree building and combining the trees together. In some examples, a majority vote of the resulting trees' predictions can be used to generate produce a final Random Forest prediction 414 from a forest of underlying trees.

A deep learning model 408 can be a base predictive model 304 that outputs a deep learning prediction 416. A deep learning prediction 416 can be a base prediction 306 of costs, utilization, risk metrics, and/or other information about a member 102.

Deep learning models 408 can be based on neural networks. For example, a deep learning model 408 can include a multi-layer, feedforward network of neurons, where each neuron takes a weighted combination of input signals as shown in Equation 8:

$\alpha=\Sigma_{i=1}^n w_i x_i+b.$  (Eq. 8)

Equation 8 reflects a weighted sum of input covariates, with additional bias b, the neuron's activation threshold. The neuron can produce an output, $f(\alpha)$, that represents a non-linear activation function. In the overall neural network, an input layer can match the covariate space, and can be followed by multiple layers of neurons to produce abstractions from input data, ending with a classification layer to match a discrete set of outcomes. Each layer of neurons can provide inputs to the next layer, and weights and bias values can determine the output from the neural network. In some examples, learning can involve adapting such weights to minimize a mean squared error between the predicted outcome and the observed outcome, across individuals in the derivation dataset.

Deep learning estimators can be developed by training across multiple activation functions and hidden layer sizes. Such activation functions can, for example, include "max out," "rectifier," or "tanh." In some examples, a max out activation function can be a generalization of a rectified linear function given by Equation 9:

$f(\alpha)=\max(0,\alpha), f(\cdot)\in R_+.$  (Eq. 9)

For example, in a max out activation function, each neuron can choose the largest output of two input channels, where each input channel has a weight and bias value. In some examples, "dropout" can be used, in which the function is constrained so that each neuron in the neural network suppresses its activation with probability P (<0.2 for input neurons, and <0.5 for hidden neurons), which scales network weight values towards 0 and can cause each training iteration to train a different estimator, thereby enabling exponentially larger numbers of estimators to be averaged as an ensemble to prevent overfitting and improve generalization. A rectifier activation function can be a version of the max out activation function in which the output of one channel is always zero.

In some examples, a deep learning model 408 can assign different variables, such as ages of members 102, diagnoses of members 102, prescriptions of members 102, and/or other factors to different columns. The deep learning model 408 can identify which of those variables, and/or which combinations of variables, are most predictive of actual results in a training dataset, such as incurred healthcare costs and visits to healthcare providers.

As shown in FIG. 4, a GBM meta-learner 418 can be a prediction combination model 308 that combines one or more linear model predictions 410 from one or more regularized linear models 402, one or more GBM predictions 412 from one or more GBM models 404, one or more Random Forest predictions 414 from one or more Random Forest models 406, and/or one or more deep learning predictions 416 from one or more deep learning models 408 into a final prediction 114.

The GBM meta-learner 418 may use Gradient Boosting Machine techniques to determine weights 310 for different instances of base predictive models 304, and use those weights 310 to combine corresponding base predictions 306 into a final prediction 114. For example, the GBM meta-learner 418 can select linear model weights 420 for corresponding regularized linear models 402, select GBM weights 422 for corresponding GBM models 404, select Random Forest weights 424 for corresponding Random Forest models 406, and select deep learning weights 426 for corresponding deep learning models 408. The GBM meta-learner 418 can use the linear model weights 420, GBM weights 422, Random Forest weights 424, and deep learning weights 426 to generate the prediction 114 using weighted averages, or other weighted combinations, of associated linear model predictions 410, GBM predictions 412, Random Forest predictions 414, and deep learning predictions 416.

Over time, as ticket feedback 118 is received from representatives 104, the GBM meta-learner 418 may adjust the linear model weights 420, GBM weights 422, Random Forest weights 424, and deep learning weights 426. Accordingly, if ticket feedback 118 shows over time that one or more of the regularized linear models 402, GBM models 404, Random Forest models 406, or deep learning models 408 generate base predictions 306 with priority levels that more closely match the ticket feedback 118 from representatives 104, the better-performing predictive models can be up-weighted and the worse-performing predictive models can be down-weighted. Accordingly, future predictions 114 generated based on the adjusted weights 310 may have outreach priorities that are closer to how representatives 104 would rank their outreach priorities, and member outreach services can be offered to corresponding members 102 in a more timely manner and/or in a more effective order.

Figure 5:
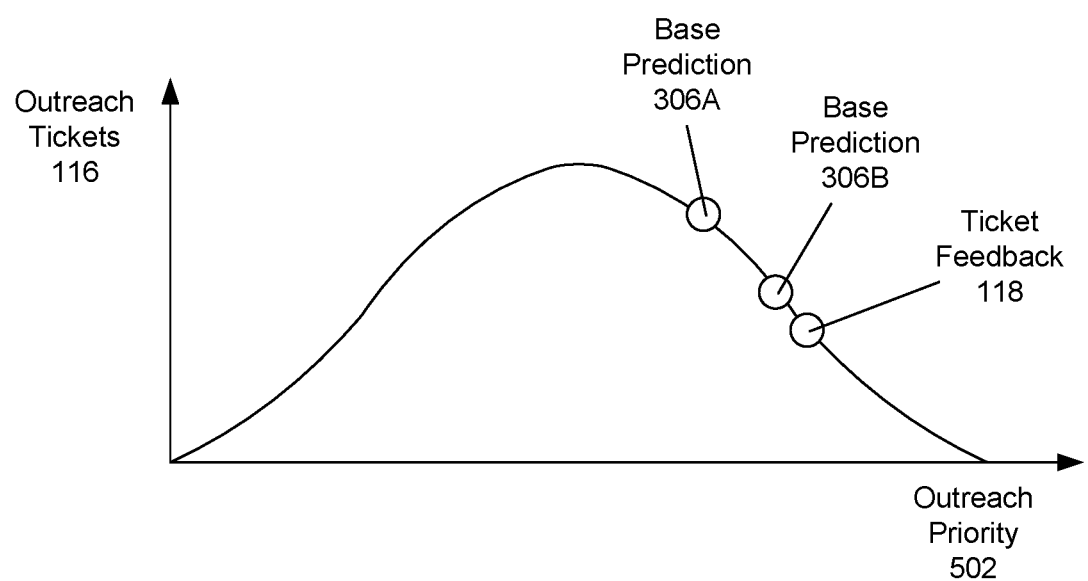
FIG. 5 depicts an example of a curve that can be used by a prediction combination model to determine relative outreach priorities associated with base predictions and/or ticket feedback.

FIG. 5 depicts an example of a curve that can be used by a prediction combination model 308 to determine relative outreach priorities 502 associated with base predictions 306 and/or ticket feedback 118. As discussed above, base predictions 306 and final predictions 114 can include cost estimates, utilization estimates, risk metric estimates, and/or other information associated with members 102. The information in base predictions 306 and final predictions 114 can be used to determine an outreach priority 502 for associated outreach tickets 116. For example, when a first prediction 114 indicates that a first member's costs, utilizations, and/or risk metrics are expected to rise sharply, and a second member's costs, utilizations, and/or risk metrics are expected to rise more slowly, the prediction engine 110 or the ticket manager 112 may determine that an outreach ticket 116 associated with the first member 102 has a greater outreach priority 502 than an outreach ticket 116 associated with the second member 102. Accordingly, the ticket manager 112 may arrange a queue of outreach tickets 116 based on corresponding metrics of outreach priorities 502.

In some examples, the outreach priority 502 associated with a set of outreach tickets 116 can be scaled to a bell curve as shown in FIG. 5. For example, outreach priorities 502 of a set of outreach tickets 116 can be scaled into a Z-score bell curve with a mean of zero and a standard deviation of 1. On such a bell curve, most outreach tickets 116 may fall near the center of the bell curve. However, some outreach tickets 116 may fall in high-priority ranges that indicate that it may be more critical to contact corresponding members 102 to offer member outreach services than other members 102 whose outreach tickets 116 have lower scaled outreach priorities 502. Although outreach priorities 502 of outreach tickets 116 can be based on final predictions 114 generated using a weighted combination of multiple base predictions 306, scaled outreach priorities 502 that individual base predictions 306 would have had alone can also be plotted on such a bell curve.

Ticket feedback 118 can also be scaled to the same bell curve. As discussed above, in some examples, ticket feedback 118 may be based on intervenability scores, interpretability scores, and/or a combination of both scores. For instance, if a representative 104 rates an outreach ticket 116 with an intervenability score of three out of five and an interpretability score of four out of five, the ticket feedback 118 can overall rate the outreach ticket 116 with as a seven out of ten on an outreach priority 502 scale. Such scores in ticket feedback 118 can be scaled to the same Z-score bell curve discussed above with respect to outreach tickets 116, even if outreach tickets 116 are prioritized in queues based on predicted rises in costs, utilizations, risk metrics, and/or other outreach priority 502 factors.

The prediction combination model 308 can determine how closely the scaled ticket feedback 118 matches the scaled outreach priorities 502 associated with base predictions 306 generated by different base predictive models 304. The prediction combination model 308 can adjust weights 310 associated with the base predictive models 304 upward or downward, based on how closely the scaled outreach priority 502 associated with the base predictive models 304 matched the scaled ticket feedback 118.

For example, FIG. 5 shows that base prediction 306B for a member 102 had a scaled outreach priority 502 that was closer to the scaled outreach priority 502 of actual ticket feedback 118 associated with that member's outreach ticket 116 than base prediction 306A. The prediction combination model 308 may accordingly adjust weights 310 by down-weighting a first base predictive model 304A that generated base prediction 306A and/or up-weighting a second base predictive model 304B that generated better-performing base prediction 306B. Base predictions 306 from both the first base predictive model 304A and the second base predictive model 304B can continue to be used to generate final predictions in the prediction engine 110 according to the adjusted weights 310.

As noted above, machine-learning and/or artificial intelligence can also, or alternately, be used to adjust weights 310 of different base predictive models 304. For example, as discussed above with respect to FIG. 4, a GBM meta-learner 418 can evaluate how closely elements of base predictions 306 matched elements of later-received ticket feedback 118, and adjust corresponding weights 310 of base predictive models 304 up or down accordingly.

Figure 6:
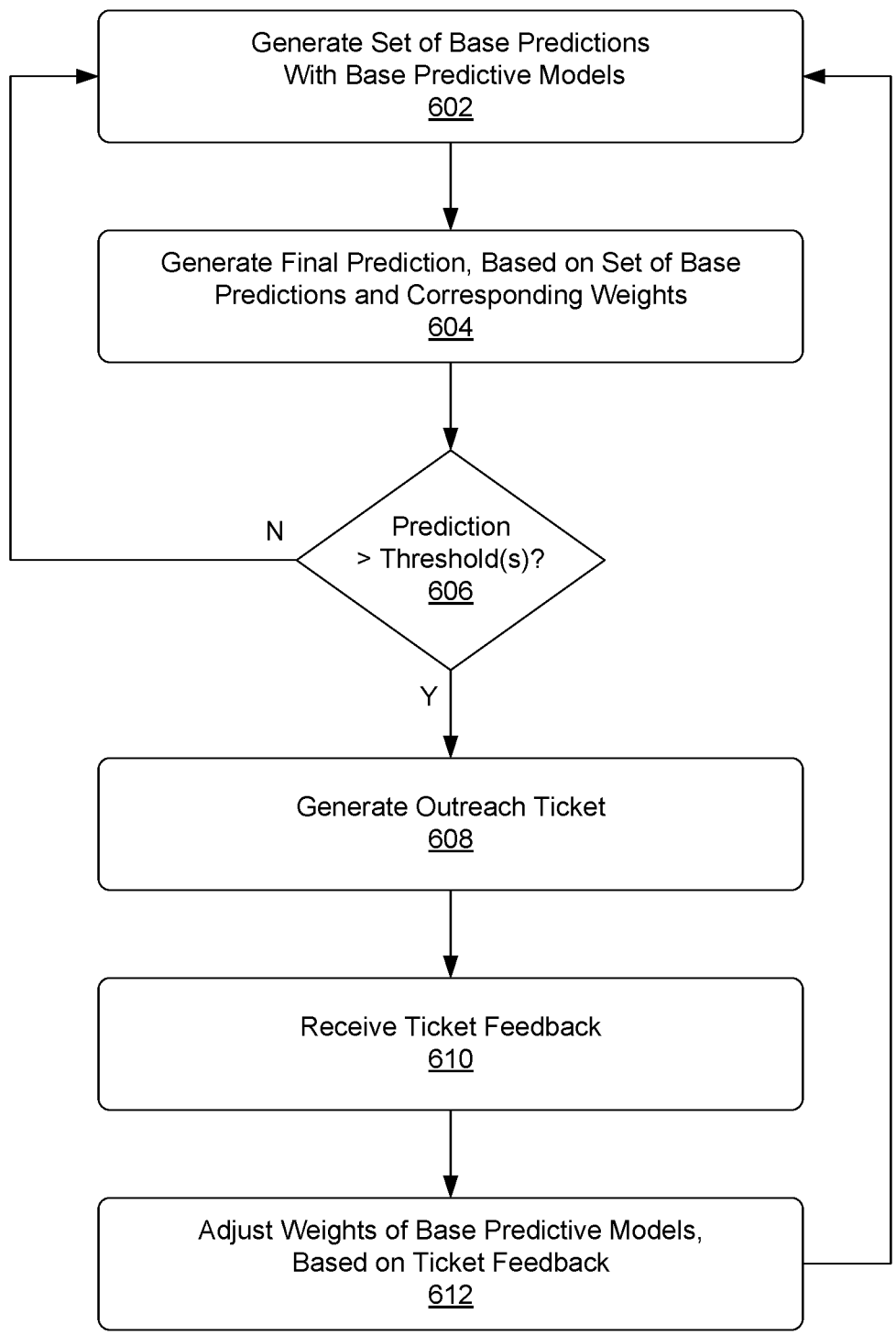
FIG. 6 shows a flowchart of an example method for generating predictions and outreach tickets, and for adjusting weights in a prediction engine according to ticket feedback.

FIG. 6 shows a flowchart of an example method for generating predictions 114 and outreach tickets 116, and for adjusting weights 310 in a prediction engine 110 according to ticket feedback 118. At block 602, a prediction engine 110 can generate a set of base predictions 306 using an ensemble of base predictive models 304. As discussed above, the ensemble of base predictive models 304 may include multiple types of base predictive models 304, and/or include multiple instances of each type of base predictive model 304. Different instances of base predictive models 304 can be trained on different random subsets of data from one or more healthcare data repositories 108. At block 602, the ensemble of base predictive models 304 can generate base predictions 306 for a member 102 based on data in one or more healthcare data repositories 108.

At block 604, a prediction combination model 308 in the prediction engine 110, such as a meta-learner, can combine the base predictions 306 into a final prediction 114 for the member 102, based on weights 310 associated with the base predictive models 304 that generated the base predictions 306. For instance, in some examples, the prediction combination model 308 can generate a final prediction 114 for a member 102 as a weighted average of the base predictions 306, with the contributions of the base predictions 306 to the final prediction 114 being based on corresponding weights 310.

At block 606, the prediction engine 110 or a ticket manager 112 can determine if the final prediction 114 includes one or more values that meet or exceed corresponding threshold values. For example, the prediction 114 can include a predicted estimate of a rise or decrease in healthcare costs associated with the member 102 over a period of time, relative to previous periods of time. In this example, the prediction engine 110 or the ticket manager 112 may determine if the prediction 114 indicates a rise in costs that exceeds a predefined threshold value. As another example, the prediction 114 can include a predicted utilization estimate of a number of visits the member 102 will make to healthcare providers in total, or by category, over a period of time. In this example, the prediction engine 110 or the ticket manager 112 may determine if the prediction 114 indicates that a predicted number of visits to healthcare providers in total, or in one or more categories, by the member 102 over a period of time exceeds a predefined threshold value. As yet another example, the prediction 114 can include predictions of one or more risk metrics, such as risks or admission or readmission to hospitals or other healthcare facilities, risks of pharmaceutical advancement to more expensive medications and/or to medications with increased side effects, risk of increased suffering levels, risks of increased mortality, and/or predictions of other types of future risks. In this example, the prediction engine 110 or the ticket manager 112 can determine if the prediction 114 indicates a predicted rise in one or more risk metrics that exceeds a predefined threshold value.

If the prediction engine 110 or the ticket manager 112 determines at block 606 that one or more values in a prediction 114 exceed one or more threshold values, the ticket manager 112 can generate an outreach ticket 116 for the member 102 at block 608. For example, if a prediction 114 indicates that healthcare costs associated with a member 102 are expected to rise more than a threshold amount over the next year (e.g., the prediction 114 meets or exceeds a threshold), an outreach ticket 116 can be generated such that a representative 104 can attempt to contact the member 102 to offer member outreach services. However, if values in a prediction 114 for a member 102 do not meet or exceed one or more threshold values at block 606, the process can return to block 602 and the prediction engine 110 can continue generating base predictions 306 for the same member 102 and/or other members 102. For example, if a prediction 114 indicates that costs, utilizations, or risk metrics associated with a member 102 are expected to decrease relative to previous levels, or are expected to rise at less than a threshold amount, there may be little or no benefit to offering member outreach services to that member 102.

In some examples, blocks 602 through 608 can be performed multiple times for multiple members 102, such that outreach tickets 116 for different members 102 can be generated at block 608. As discussed above, a set of outreach tickets 116 for different members 102 can be prioritized or ordered for one or more representatives 104, for example in a queue of outreach tickets 116. In some examples, outreach tickets 116 can be prioritized based on corresponding outreach priority 502 metrics. Accordingly, representatives 104 may attempt to contact members 102 in an order based on priorities of corresponding outreach tickets 116, such that members 102 who may benefit more from member outreach services, who are better candidates for member outreach services, and/or whose situations are better explained by outreach tickets 116 may be prioritized to be contacted before other members 102.

At block 610, after representatives 104 have at least attempted to contact members 102 identified in outreach tickets 116, the ticket manager 112 and/or the prediction engine 110 can receive ticket feedback 118 from the representatives 104. As discussed above, ticket feedback 118 may be received from a representative 104 via a survey, form, user interface, or other mechanism. Ticket feedback 118 may provide scores, rankings, or other feedback from representatives 104 in one or more categories, such as categories for how "intervenable" a member 102 identified in an outreach ticket 116 was, and/or how "interpretable" information in the outreach ticket 116 itself was. For example, intervenability and/or interpretability scores can be provided by representatives on a Likert scale of 0-5, or other scale. In some examples, ticket feedback 118 can be a combination of both intervenability and interpretability scores on a 0-10 scale, or other scale.

At block 612, the prediction combination model 308 can use the ticket feedback 118 received at block 610 to adjust weights 310 corresponding to different base predictive models 304. For example, an outreach ticket 116 may have been prioritized as the second-highest priority in a set of outreach tickets 116, but ticket feedback 118 associated with the set of outreach tickets 116 may indicate that representatives 104 gave that outreach ticket 116 the tenth-highest score of the set of outreach tickets 116. Accordingly, the prediction combination model 308 may increase weights 310 associated with base predictive models 304 that produced base predictions 306 that, taken alone, were closest to ranking member outreach to the member 102 as the tenth-highest among base predictions 306 for a set of members 102. The prediction combination model 308 may similarly decrease weights 310 associated with base predictive models 304 that produced base predictions 306 that were farther away from ranking a member 102 as being the tenth-highest priority for member outreach services.

As a non-limiting example, a seventh instance of a GBM model 404 may have produced GBM predictions 412 for a set of members 102, and those GBM predictions 412 may include values indicating that a particular member 102 is the second-highest priority for member outreach services, out of the set of members 102. In this example, a fifty-fifth instance of a deep learning model 408 may have produced deep learning predictions 416 for the same set of members 102.

These deep learning predictions 416 may include values indicating that the particular member 102 was the fifteenth-highest priority out of the set of members 102. The GBM predictions 412 and the deep learning predictions 416 can be combined, along with other base predictions 306 from other base predictive models 304 using corresponding weights 310, into final predictions 114 for the set of members 102, and corresponding outreach tickets 116 can be generated. If ticket feedback 118 then indicates that representatives 104 subjectively felt that, among the set of members 102, the particular member 102 was the third-most suitable for member outreach services. In this example, the prediction combination model 308 may determine that the GBM predictions 412 of the seventh instance of the GBM model 404 (indicating that the member 102 was the second-highest priority) more closely matched the ticket feedback 118 (indicating that the member 102 was the third-highest priority) than the deep learning predictions 416 fifty-fifth instance of the deep learning model 408 (indicating that the member 102 was the fifteenth-highest priority). Accordingly, the prediction combination model 308 can increase the weight 310 associated with the seventh instance of the GBM model 404 and decrease the weight 310 associated with the fifty-fifth instance of the deep learning model 408.

Over time, through the example process of FIG. 6, ticket feedback 118 can be used to increase the weights 310 of base predictive models 304 that tend to produce base predictions 306 that would prioritize members 102 for member outreach services similarly to how representatives 104 would prioritize such members 102. Similarly, ticket feedback 118 can be used to decrease the weights 310 of base predictive models 304 that tend to produce base predictions 306 that would prioritize members 102 for member outreach services in orders that least match how representatives 104 would prioritize such members 102. Base predictions 306 from numerous base predictive models 304 can continue to be combined into final predictions 114. However, the contribution of base predictive models 304 that least match ticket feedback 118 to the final prediction 114 can be lessened according to the adjusted weights 310, and the contribution of base predictive models 304 that most match ticket feedback 118 to the final prediction 114 can be increased according to the adjusted weights 310. This process can accordingly improve the quality, accuracy, and/or priorities of final prediction 114 and corresponding outreach tickets 116, relative to equally weighting different base predictions 306 from different instances of base predictive models 304 and/or different types of base predictive models 304.

Figure 7:
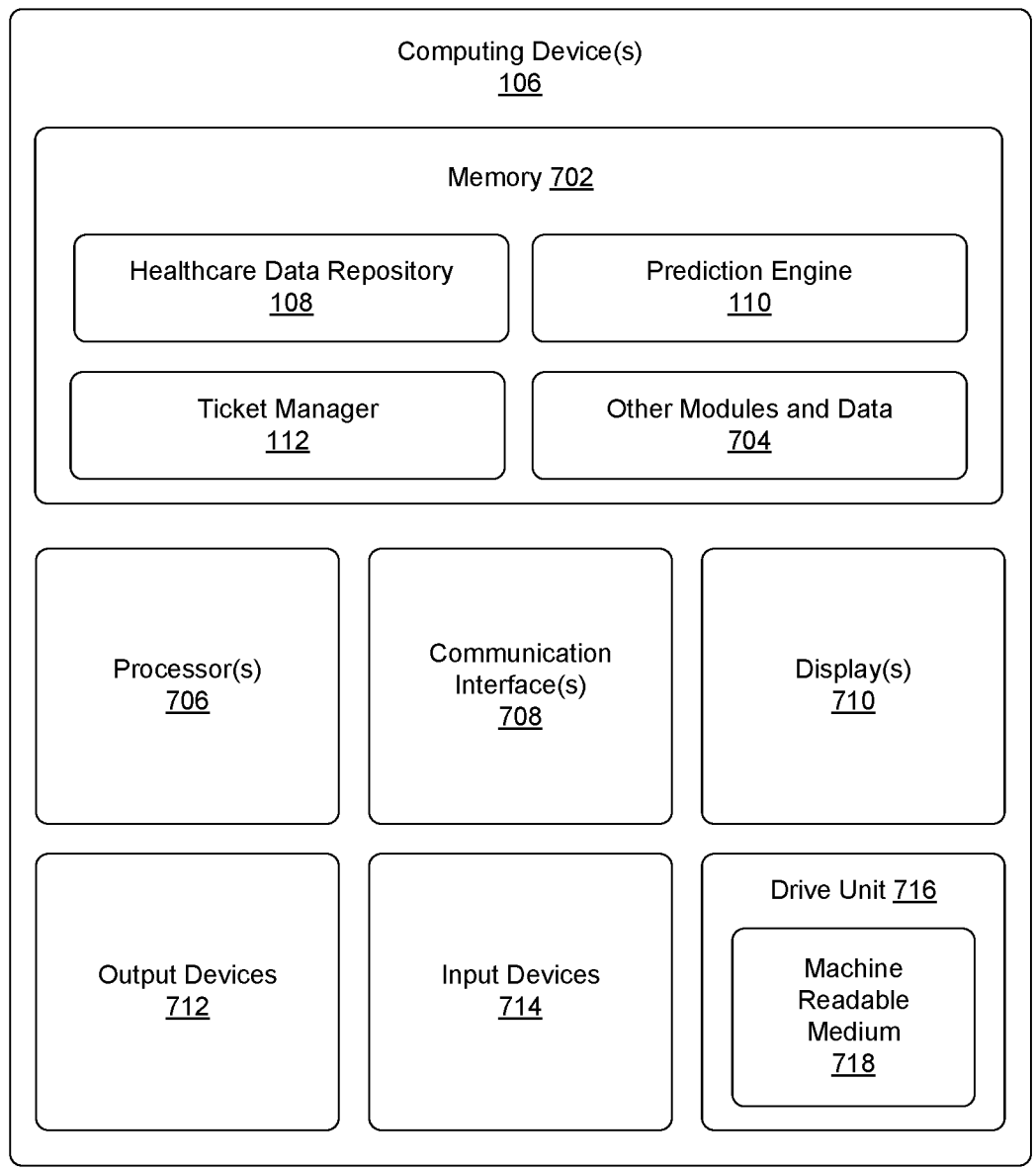
FIG. 7 shows an example system architecture for a computing device associated with a member outreach system.

FIG. 7 shows an example system architecture for a computing device 106 associated with the member outreach system 100 described herein. A computing device 106 can be a server, computer, cloud computing device, or other type of computing device that executes at least a portion of the member outreach system 100. In some examples, elements of the member outreach system 100 can be distributed among, and/or be executed by, multiple computing devices 106. For example, the prediction engine 110 may execute on a different computing device 106 than the ticket manager 112. In other examples, the prediction engine 110 can execute on the same computing device 106 as the ticket manager 112.

A computing device 106 can include memory 702. In various examples, the memory 702 can include system memory, which may be volatile (such as RAM), nonvolatile (such as ROM, flash memory, etc.) or some combination of the two. The memory 702 can further include non-transitory computer-readable media, such as volatile and nonvolatile, removable and non-removable media implemented in any method or technology for storage of information, such as computer readable instructions, data structures, program modules, or other data. System memory, removable storage, and non-removable storage are all examples of non-transitory computer-readable media. Examples of non-transitory computer-readable media include, but are not limited to, RAM, ROM, EEPROM, flash memory or other memory technology, CD-ROM, digital versatile discs (DVD) or other optical storage, magnetic cassettes, magnetic tape, magnetic disk storage or other magnetic storage devices, or any other non-transitory medium which can be used to store desired information and which can be accessed by one or more computing devices 106 associated with the member outreach system 100. Any such non-transitory computer-readable media may be part of the computing devices 106.

The memory 702 can store data, computer-readable or computer-executable instructions, and/or other information associated with the member outreach system 100. For example, the memory 702 can store data and/or instructions associated with the healthcare data repository 108, prediction engine 110, and ticket manager 112 discussed above. The memory 702 may also store other modules and data 704 that can be utilized by the computing device 106 to perform or enable performing any action taken by the member outreach system 100. Such other modules and data 704 can include a platform, operating system, and applications, and data utilized by the platform, operating system, and applications.

One or more computing devices 106 of the member outreach system 100 can also have processor(s) 706, communication interfaces 708, displays 710, output devices 712, input devices 714, and/or a drive unit 716 including a machine readable medium 718.

In various examples, the processor(s) 706 can be a central processing unit (CPU), a graphics processing unit (GPU), both a CPU and a GPU, or any other type of processing unit. Each of the one or more processor(s) 706 may have numerous arithmetic logic units (ALUs) that perform arithmetic and logical operations, as well as one or more control units (CUs) that extract instructions and stored content from processor cache memory, and then executes these instructions by calling on the ALUs, as necessary, during program execution. The processor(s) 706 may also be responsible for executing computer applications stored in the memory 702, which can be associated with common types of volatile (RAM) and/or nonvolatile (ROM) memory.

The communication interfaces 708 can include transceivers, modems, interfaces, antennas, telephone connections, and/or other components that can transmit and/or receive data over networks, telephone lines, or other connections.

The display 710 can be a liquid crystal display or any other type of display commonly used in computing devices. For example, a display 710 may be a touch-sensitive display screen, and can then also act as an input device or keypad, such as for providing a soft-key keyboard, navigation buttons, or any other type of input.

The output devices 712 can include any sort of output devices known in the art, such as a display 710, speakers, a vibrating mechanism, and/or a tactile feedback mechanism. Output devices 712 can also include ports for one or more peripheral devices, such as headphones, peripheral speakers, and/or a peripheral display.

The input devices 714 can include any sort of input devices known in the art. For example, input devices 714 can include a microphone, a keyboard/keypad, and/or a touch-sensitive display, such as the touch-sensitive display screen described above. A keyboard/keypad can be a push button numeric dialing pad, a multi-key keyboard, or one or more other types of keys or buttons, and can also include a joystick-like controller, designated navigation buttons, or any other type of input mechanism.

The machine readable medium 178 can store one or more sets of instructions, such as software or firmware, that embodies any one or more of the methodologies or functions described herein. The instructions can also reside, completely or at least partially, within the memory 702, processor(s) 706, and/or communication interface(s) 708 during execution thereof by the one or more computing devices 106 of the member outreach system 100. The memory 702 and the processor(s) 706 also can constitute machine readable media 718.

Although the subject matter has been described in language specific to structural features and/or methodological acts, it is to be understood that the subject matter is not necessarily limited to the specific features or acts described above. Rather, the specific features and acts described above are disclosed as example embodiments.

What is claimed is:

1. A computer-implemented method, comprising:
    training, by one or more processors, a set of machine learning models to identify features in historical healthcare data that are predictive of at least one of historical healthcare costs, historical healthcare utilizations, or historical risk metrics indicated in the historical healthcare data, wherein different machine learning models, of the set of machine learning models, vary based on at least one of:
    being different types of machine learning models, or
    being trained on different subsets of the historical healthcare data;
    generating, by the one or more processors and using the set of machine learning models, a set of base predictions associated with a member of a health plan based on the features in healthcare data associated with the member, wherein:
        the different machine learning models, of the set of machine learning models, generate different base predictions of the set of base predictions,
        the set of base predictions indicate at least one of:
            predicted healthcare costs associated with the member,
            predicted healthcare utilizations associated with the member, or
            predicted risk metrics associated with the member, and
        the different base predictions indicate one or more outreach priority levels associated with the member;
    generating, by the one or more processors, a final prediction associated with the member by combining the set of base predictions based at least in part on a set of weights that correspond to the set of machine learning models;
    generating, by the one or more processors, an outreach ticket associated with the member based on the final prediction;
    causing, by the one or more processors, the outreach ticket to be sent to a computing device operable by a representative;
    receiving, by the one or more processors, ticket feedback associated with the outreach ticket from the computing device, wherein the ticket feedback indicates at least one score, subjectively assigned by the representative, including one or more of:
        an outreach intervenability score of the member, or
        an interpretability score of the outreach ticket; and
    adjusting, by the one or more processors, the set of weights, by using a prediction combination model to increase or decrease individual weights, of the set of weights, that correspond to the different machine learning models, based on correlations between the at least one score indicated in the ticket feedback and the one or more outreach priority levels indicated by the different base predictions generated by the different machine learning models.

2. The computer-implemented method of claim 1, wherein the healthcare data includes enrollment data associated with the member, claim data associated with the member, and at least one of demographic data for a geographic location associated with the member, provider data associated with the geographic location or the member, or engagement data associated with a use by the member of a website or mobile application associated with the health plan.

3. The computer-implemented method of claim 1, wherein at least one of the historical healthcare data and the healthcare data associated with the member is stored in a healthcare data repository indexed at one or more of a member level and a provider level.

4. The computer-implemented method of claim 1, wherein the different types of machine learning models include two or more of regularized linear models, Gradient Boosting Machine Models, Random Forest Models, or deep learning models.

5. The computer-implemented method of claim 1, wherein the prediction combination model is a Gradient Boosting Machine meta-learner.

6. The computer-implemented method of claim 1, wherein the final prediction indicates at least one of a total cost estimate for the member over a period of time, an estimated change in costs for the member over the period of time, a utilization value indicating an estimated number of visits to one or more healthcare providers over the period of time, or a predicted change to one or more risk metrics associated with the member.

7. The computer-implemented method of claim 6, further comprising:
    determining, by the one or more processors, that the total cost estimate, the estimated change in costs, the utilization value, or the predicted change to the one or more risk metrics exceeds a threshold value; and
    generating, by the one or more processors, the outreach ticket based on determining that the total cost estimate, the estimated change in costs, the utilization value, or the predicted change to the one or more risk metrics exceeds the threshold value.

8. The computer-implemented method of claim 1, wherein the outreach ticket is provided to the representative in a queue of outreach tickets ordered based on outreach priorities determined based on the final prediction and corresponding final predictions of other outreach tickets in the queue.

9. The computer-implemented method of claim 1, wherein the outreach ticket identifies one or more attributes of the member, based on key variables identified as being predictive in the set of base predictions or the final prediction.

10. The computer-implemented method of claim 9, wherein generating the outreach ticket comprises selecting, by the one or more processors, values for an outreach ticket template based on the key variables.

11. The computer-implemented method of claim 1, wherein the different machine learning models, of the set of machine learning models, is trained based on the historical healthcare data until a corresponding area under the curve statistic (C-statistic) meets a threshold value.

12. A system, comprising:
one or more processors; and
memory storing a healthcare data repository of data including historical healthcare data and healthcare data associated with a member of a health plan, the memory further storing computer-executable instructions that, when executed by the one or more processors, cause the one or more processors to perform operations comprising:
training a set of machine learning models to identify features in historical healthcare data that are predictive of at least one of historical healthcare costs, historical healthcare utilizations, or historical risk metrics indicated in the historical healthcare data, wherein different machine learning models, of the set of machine learning models, vary based on at least one of:
being different types of machine learning models, or
being trained on different subsets of the historical healthcare data;
generating, using the set of machine learning models, a set of base predictions associated with the member based on the features in the healthcare data associated with the member, wherein:
the different machine learning models, of the set of machine learning models, generate different base predictions of the set of base predictions,
the set of base predictions indicate at least one of:
predicted healthcare costs associated with the member,
predicted healthcare utilizations associated with the member, or
predicted risk metrics associated with the member, and
the different base predictions indicate one or more outreach priority levels associated with the member;
generating a final prediction associated with the member by combining the set of base predictions based at least in part on a set of weights that correspond to the set of machine learning models;
generating an outreach ticket associated with the member based on the final prediction;
providing the outreach ticket to a computing device operable by a representative;
receiving ticket feedback associated with the outreach ticket from the computing device, wherein the ticket feedback indicates at least one score, subjectively assigned by the representative, including one or more of:
an outreach intervenability score of the member, or
an interpretability score of the outreach ticket; and
adjusting the set of weights by using a prediction combination model to increase or decrease individual weights, of the set of weights, that correspond to the different machine learning models, based on correlations between the at least one score indicated in the ticket feedback and the one or more outreach priority levels indicated by the different base predictions generated by the different machine learning models.

13. The system of claim 12, wherein the healthcare data associated with the member includes enrollment data associated with the member, claim data associated with the member, and at least one of demographic data for a geographic location associated with the member, provider data associated with the geographic location or the member, or engagement data associated with a use by the member of a website or mobile application associated with the health plan.

14. The system of claim 12, wherein the outreach ticket identifies one or more attributes of the member, based on key variables identified as being predictive in the set of base predictions or the final prediction.

15. The system of claim 12, wherein the prediction combination model is a Gradient Boosting Machine metalearner.

16. One or more non-transitory computer-readable media storing computer-executable instructions that, when executed by one or more processors of at least one computing device, cause the one or more processors to perform operations comprising:
training a set of machine learning models to identify features in historical healthcare data that are predictive of at least one of historical healthcare costs, historical healthcare utilizations, or historical risk metrics indicated in the historical healthcare data, wherein different machine learning models, of the set of machine learning models, vary based on at least one of:
being different types of machine learning models, or
being trained on different subsets of the historical healthcare data;
generating a set of base predictions associated with a member of a health plan using the set of machine learning models, wherein:
the set of machine learning models generates the set of base predictions using the features in healthcare data associated with the member,
the set of base predictions indicate at least one of:
predicted healthcare costs associated with the member,
predicted healthcare utilizations associated with the member, or
predicted risk metrics associated with the member, and
individual base predictions, of the set of base predictions, indicate corresponding outreach priority levels associated with the member;
generating a final prediction associated with the member by combining the set of base predictions, based at least in part on a set of weights that correspond to the set of machine learning models, wherein the set of weights is determined by a prediction combination model based at least in part on correlations between:
outreach intervenability scores indicated in subjective representative feedback associated with past member outreach services offered by representatives to other members, and
previous outreach priority levels associated with previous base predictions, associated with the other members, generated by the different machine learning models of the set of machine learning models; and
generating a notification associated with the member based on the final prediction.

17. The one or more non-transitory computer-readable media of claim 16, wherein the notification is an outreach ticket, and the operations further comprise:

causing the outreach ticket to be sent to a representative computing device operable by a representative;

receiving new subjective representative feedback associated with the outreach ticket from the representative computing device; and adjusting the set of weights, by the prediction combination model, based on correlations between a new outreach intervenability score indicated in the new subjective representative feedback and the outreach priority levels indicated by the individual base predictions generated by the different machine learning models of the set of machine learning models.

18. The one or more non-transitory computer-readable media of claim 17, wherein the prediction combination model is a Gradient Boosting Machine meta-learner.

19. The one or more non-transitory computer-readable media of claim 16, wherein the notification is an automated notification, and the operations further comprise sending the automated notification to a computing device associated with the member.

20. The one or more non-transitory computer-readable media of claim 16, wherein the healthcare data associated with the member includes enrollment data associated with the member, claim data associated with the member, and at least one of demographic data for a geographic location associated with the member, provider data associated with the geographic location or the member, or engagement data associated with a use by the member of a website or mobile application associated with the health plan.

* * * * *